US008012985B2

(12) United States Patent
Vial et al.

(10) Patent No.: US 8,012,985 B2
(45) Date of Patent: Sep. 6, 2011

(54) COMPOUNDS WITH ANTIPARASITIC ACTIVITY AND MEDICINES CONTAINING SAME

(75) Inventors: Henri Vial, Montpellier (FR); Michele Calas, Montpellier (FR); Roger Escale, Grabels (FR); Valerie Vidal, Montpellier (FR); Francoise Bressolle, Montpellier (FR); Marie-Laure Ancelin, St. Jean de Cuculles (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 1559 days.

(21) Appl. No.: 10/521,329

(22) PCT Filed: Jul. 18, 2003

(86) PCT No.: PCT/FR03/02283
§ 371 (c)(1),
(2), (4) Date: Apr. 25, 2005

(87) PCT Pub. No.: WO2004/009068
PCT Pub. Date: Jan. 29, 2004

(65) Prior Publication Data
US 2005/0176819 A1    Aug. 11, 2005

(30) Foreign Application Priority Data
Jul. 18, 2002   (FR) .................................... 02 09156

(51) Int. Cl.
*C07D 401/06*    (2006.01)
*C07D 403/06*    (2006.01)
*C07D 403/12*    (2006.01)
*C07D 413/06*    (2006.01)
*C07C 249/02*    (2006.01)
*C07C 257/14*    (2006.01)
*C07C 257/22*    (2006.01)
*C07F 9/40*    (2006.01)
*A61K 31/155*    (2006.01)
*A61K 31/4178*    (2006.01)
*A61K 31/4184*    (2006.01)
*A61K 31/4245*    (2006.01)
*A61K 31/506*    (2006.01)
*A61K 31/662*    (2006.01)
*A61P 33/06*    (2006.01)

(52) U.S. Cl. ........ 514/256; 514/275; 514/364; 514/397; 514/633; 514/634; 514/636; 544/296; 548/131; 548/312.7; 548/557; 548/558; 564/229; 564/236; 564/243

(58) Field of Classification Search .................... None
See application file for complete search history.

(56) References Cited

U.S. PATENT DOCUMENTS 2,744,116 A * 5/1956 Shreve et al. ............... 548/265.6
3,222,285 A * 12/1965 Rai et al. ....................... 510/402
3,471,509 A   10/1969 McKillip
5,242,948 A * 9/1993 Mueller et al. ................ 514/635

FOREIGN PATENT DOCUMENTS

CH     214 041 A       3/1941
EP    0 472 093 A       2/1992
FR    1 542 163 A      10/1968
JP    57 048902 A       3/1982

OTHER PUBLICATIONS

Chapman et al., Journal of the Chemical Society, Chemical Communications, (7), 240-241, 1976.*
Lamb et al., Journal of the Chemical Society, 1253-1257, 1939.*
Oxley et al., Journal of the Chemical Society, 497-506, 1947.*
CAS Registry No. 334785-11-4, entered STN on May 7, 2001.*
B.H. King. "New Trypanocidal Substances". The Lancet. vol. 223. Dec. 11, 1937, pp. 1360-1363.
Patent Abstracts of Japan. vol. 006, No. 122. Jul. 7, 1982.
E.M. Lourie. "Studies in chemotherapy. XXII. The action of certain aromatic diamidines on *Babesia canis* infections of puppies", Tropical Diseases Bulletin. vol. 37. No. 6. 1940. pp. 405-406.
S.R. Christophers, "Observations on the Coures of *Plasmodium knowlesi* Infection in Monkeys (Macacus Rhesus), with Notes on its Treatment by (1) Atebrin and (2) 1:11 Normal Undecane Diamidine. Together with a Note on the Action of the Latter on Bird Malaria" Annals of Tropical Medicine and Parasitology, Academic Press. London. GB. vol. 32. 1938, pp. 257-278.
F Glyn-Hughes et al., "The Action of Undecane Diamidine in Malaria". Annals of Tropical Medicine and Parasitology, Academic Press. London, GB. vol. 32. 1938, pp. 103-107.
B. Clement. "Verbindungen zue Behandlung von Trypanosomeninfektionen". Pharmazie in Userer Zeit, 1989, Germany, vol. 18. No. 4. pp. 97-111.
Gish DT, Carpenter FH. "p-Nitrobenzyloxycarbonyl Derivatives of Amino Acids", Journal of the American Chemical Society. vol. 75. 1953. pp. 950-952.
T. Weller et al., "Orally active fibrinogen Receptor Antagonists. 2. Amidoximes as Prodrugs of Amidines", Journal of Medicinal Chemistry. American Chemical Society, Washington. US. vol. 39. 1996. pp. 3139-3147.
M. Rahmathullah Syed et al., "Prodrugs for amidines: Synthesis and anti-Pneumocystis carinii activity of carbamates of 2.5-bis (4-amidinophenyl)furan" Journal of Medicinal Chemistry, vol. 42, No. 19. Sep. 23, 1999, pp. 3994-4000.
C.A. Bell et al., "Structure-Activity Relationships of Analogs of Pentamidine Against *Plasmodium falciparum* and *Leishmania mexicana* Amazonensis". Antimicrobial Agents and Chemotherapy. American Society for Microbiology, Washington, DC. US. vol. 34. No. 7, Jul. 1990. pp. 1381-1386.
I.O Donkor et al., "Trypanocidal activity of dicationic compounds related to pentamidine", European Journal of Medicinal Chemistry. Editions Scientifique Elsevier. Paris, FR. vol. 36. No. 6, Jun. 2001. pp. 531-538.

* cited by examiner

*Primary Examiner* — Fiona T Powers
(74) *Attorney, Agent, or Firm* — Nixon & Vanderhye P.C.

(57) ABSTRACT

The invention relates to compounds having an anti-parasitic, in particular antimalarial activity, characterized in that they correspond to general formula (I)

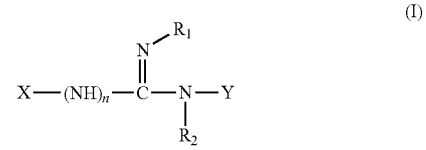

Figure 1:
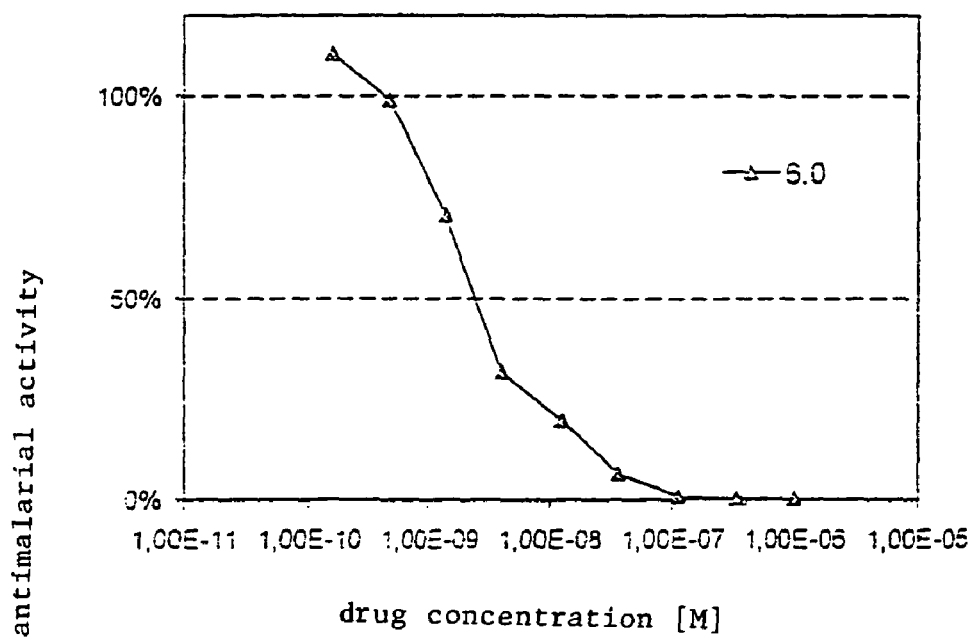

Applications in particular as compounds with anti-parasitic activity.

14 Claims, 1 Drawing Sheet

COMPOUNDS WITH ANTIPARASITIC ACTIVITY AND MEDICINES CONTAINING SAME

This application is the US national phase of international application PCT/FR2003/002283 filed 18 Jul. 2003 which designated the U.S. and claims benefit of FR 02/09156, dated 18 Jul. 2002, the entire contents of each of which are hereby incorporated by reference.

The invention relates to compounds with anti-parasitic, and more particularly antimalarial and anti-babesiosia activity.

A number of works are devoted to research into medicaments which are active against parasites and particularly against *Plasmodium*, in particular *Plasmodium falciparum*, given the range of diseases that they cause.

The inventors have observed, with certain categories of chemical compounds, a high activity, accompanied by tolerable toxicity and high bioavailability properties. Advantageously, these compounds can be administered by oral route.

An object of the invention is therefore to provide new compounds with anti-parasitic, in particular antimalarial activity.

It also relates to a process for the synthesis of such compounds.

The invention moreover relates to medicaments containing such compounds as active ingredients as well as their use and that of derivatives for making medicaments having said activities.

The compounds according to the invention are characterized in that they correspond to general formula (I)

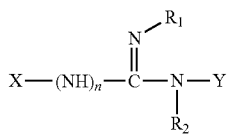
(I)

in which
either X represents a group of formula (II)

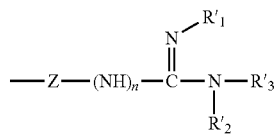
(II)

where Z is a —$(CH_2)_m$— group, with m=8 to 21,
n=0 or 1
and Y=$R_3$, $R_1$ and $R'_1$, identical to or different from one another, being chosen from H, alkyl, OH, O-alkyl, O-aryl, O—CO-alkyl, O—CO-aryl, $OSO_2$ alkyl, $OSO_2$-aryl, $OSO_2$-heterocycle, O—CO—O(or S or NH)-alkyl, O—CO—O(or S or NH)-aryl, PO(O-alky or O-aryl)$_2$, CO—O—$CH_2$aryl, cycloalkyl, $R_2$ and $R'_2$, identical to or different from one another, being chosen from H, alkyl, CO—O—$CH_2$-aryl, CO—O-alkyl, cycloalkyl, $R_3$ and $R'_3$, identical to or different from one another, representing H, alkyl, CO—O-alkyl, CO—O-aryl, COO—CH(R)—O—CO-alkyl, PO(O-alkyl or O-aryl or ONa)$_2$, CO—O—CH(R)-aryl, R being H or alkyl, or $R_1$ and $R_2$, and/or $R'_1$ and $R'_2$, or $R_2$ and $R_3$ and/or $R'_2$ and $R'_3$, together form a non aromatic mono heterocycle with the nitrogen atoms to which they are respectively attached, or also, $R_2$ and $R_3$ and/or $R'_2$ and $R'_3$ can be the same substituent, double-bonded to the nitrogen, cyclized with, respectively, $R_1$ or $R'_1$ in order to form a heterocycle, if appropriate substituted by $R_a$, which is chosen from H, alkyl, alkyl substituted by 1, 2 or 3 halogen atoms, aryl, CO—O-alkyl (or aryl), —CO—OH, —CO—$NH_2$, —CN, —CO—NH-alkyl (or aryl), —CO—N-(alkyl)$_2$, nitrogenated and/or oxygenated —CO-heterocycle, NH(H or alkyl), N(alkyl)$_2$, nitrogenated and/or oxygenated heterocycle, —O-alkyl (or aryl), —O—$CH_2$-aryl, $CH_2$N[H, (H, alkyl), (dialkyl), aryl], nitrogenated and/or oxygenated —$CH_2$-heterocycle, $CH_2$—CO—OH, either X=$R_4$ and Y represents a group of formula (III)

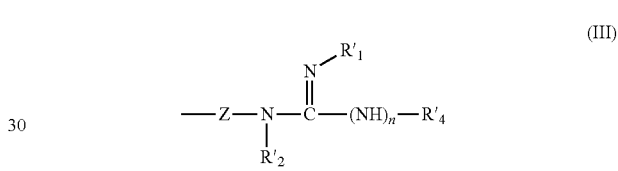
(III)

with n and Z as defined above, $R_1$ and $R'_1$, identical to or different from one another, being chosen from H, alkyl, OH, O-alkyl, O-aryl, O—CO-alkyl, O—CO-aryl, $OSO_2$-alkyl, $OSO_2$-aryl, $OSO_2$-hetrocycle, O—CO—O(or S or NH)-alkyl, O—CO—O(or S or NH)-aryl, PO(O-alkyl or O-aryl)$_2$, CO—O—$CH_2$ aryl, cycloalkyl, $R_4$ and $R'_4$ represent H, alkyl or aryl, which can be substituted by OH, O-alkyl, O-aryl, NH(H or alkyl), nitrogenated or oxygenated heterocycle, and $R_2$ and $R'_2$, identical to or different from one another, being chosen from H, alkyl, CO—O—$CH_2$-aryl, CO—O-alkyl, cycloalkyl, or $R_1$ and $R_4$ and/or $R'_1$ and $R'_4$ together form a —$(CH_2)_p$ group, p being an integer from 1 to 5, one or several hydrogen atoms being possibly replaced by a lower alkyl, and $R_2$ and $R'_2$ representing H, or $R_4$ and $R_2$ and/or $R'_4$ and $R'_2$ together form a —$(CH_2)_p$ group, one or several H being possibly changed for a lower alkyl, $R_1$ and $R'_1$ representing H, and the pharmacologically acceptable salts of these compounds, Unless otherwise specified, "aryl" designates a phenyl or any ring or heterocycle, having an aromatic character, such as the pyridine, oxazole, thiazole rings, if appropriate substituted, in particular by chlorine, —$NO_2$, —$NH_2$, N(H, alkyl) or (dialkyl);

"nitrogenated and/or oxygenated heterocycle" designates a ring with 5 or 6 vertices such as the pyrrolidine, piperidine, morpholine, piperazine, methylpiperazine rings;

"alkyl" designates a straight-chained or branched C1-C5 alkyl, if appropriate substituted by one or more halogen atoms, .$NH_2$, N(H, alkyl) or (dialkyl) amino group.

A preferred family of derivatives of the invention, or family A, corresponds to formula (IV)

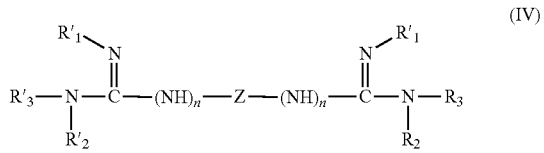

in which n, Z, $R_1$, $R'_1$, $R_2$, $R'_2$, $R_3$ and $R'_3$ are as defined above with respect to formula (II)

Advantageous compounds of this family correspond to the case where n=0 and correspond to formula (V)

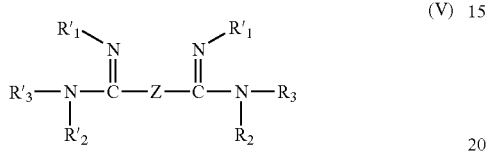

In a preferred group, or group a1, $R_1$, $R_2$ and $R_3$ and/or $R'_1$, $R'_2$ and $R'_3$ are independent of one other.

In a subgroup, $R_1$ and/or $R'_1$, and $R_2$ and/or $R'_2$ represent a hydrogen atom, $R_3$ and/or $R'_3$ being as defined above, but different from a hydrogen atom.

In another subgroup, $R_1$ and/or $R'_1$ are as defined above, but do not represent a hydrogen atom, whilst $R_3$ and/or $R'_3$, $R_2$ and/or $R'_2$ represent a hydrogen atom.

Another preferred group of compounds of formula (V) corresponds to the case where n=0 and $R_1$ and $R_2$, and/or $R'_1$ and $R'_2$ correspond to formula (VI) or group a2

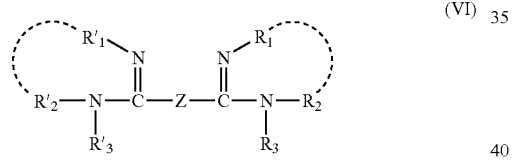

or $R_2$ and $R_3$ and/or $R'_2$ and $R'_3$ correspond to formula (VII) or group a3

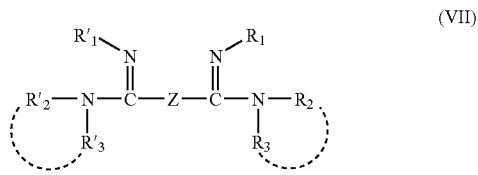

In a subgroup corresponding to formula (VI), $R_1$ and $R_2$ and/or $R'_1$ and $R'_2$ together form an —O—CO—, O—SO—, O—CS, S—CO or —S—CS group, and $R_3$ and/or $R'_3$ represent a hydrogen atom.

In another subgroup corresponding to formula (VI), $R_1$ and $R_2$, and/or $R'_1$ and $R'_2$ represent an optionally branched alkylene group and $R_3$ and/or $R'_3$ represent —CO—O-alkyl (or aryl), —CO—O—$CH_2$-aryl, CO—O—CH(alkyl)-O—CO-alkyl, PO(O-alkyl or -aryl)$_2$, alkyl or H.

In a subgroup corresponding to formula (VII), $R_1$ and/or $R'_1$ represent a hydrogen atom, and $R_2$ and $R_3$, and/or $R'_2$ and/or $R'_3$ represent a —$(CH_2)_p$— group.

Another preferred group of family A, or group a4, corresponds to the case where $R_2$ and $R_3$ and/or $R'_2$ and $R'_3$ form the same substituent and form together with $R_1$ or respectively $R'_1$ a bis-oxadiazole of formula (VIII).

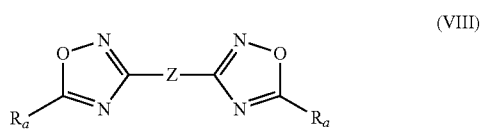

in which $R_a$ is as defined above.

In preferred compounds of this group, the halogen is advantageously F or Cl, the alkyl is a methyl or an ethyl, the aryl is a phenyl.

Another preferred family of the invention, or family B, corresponds to formula (IX)

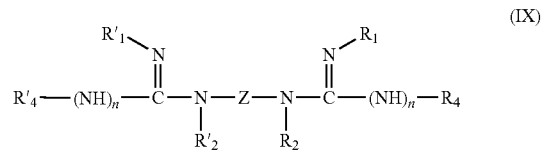

In advantageous compounds of this family, Z=—$(CH_2)_m$ and n=0, the compounds corresponding to formula (X)

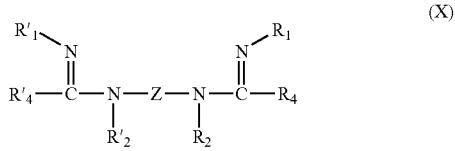

In a preferred group of family B, or group b1, the substituents are independent of one other.

In a subgroup, $R_1$ and $R_4$ and/or $R'_1$ and $R'_4$ are as defined above and $R_2$ represents a hydrogen atom.

In another subgroup, $R_1$ and $R_2$ and/or $R'_1$ and $R'_2$ together represent an oxycarbonyl chain —OCO— and $R_4$ and $R'_4$ are as defined above.

In another subgroup, $R_1$ and $R'_4$ and/or $R'_1$ and $R'_4$ together represent a —$(CH_2)_n$— group where n is an integer from 3 to 5 and $R_2$ and $R'_2$ represent H.

In yet another subgroup, $R_1$ and $R'_1$ represent H and $R_4$ and $R_2$ and/or $R'_4$ and $R'_2$ together represent a —$(CH_2)_p$— group where p is an integer from 3 to 5, one or more atoms of hydrogen can be replaced by a lower alkyl.

Another subgroup corresponds to formula (XI)

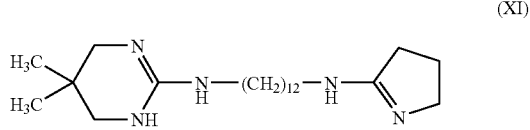

Preferred compounds of families A and B are given in Tables 1 to 3 hereafter.

TABLE 1

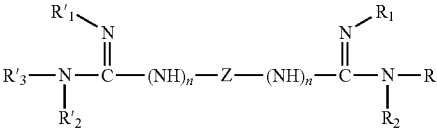

Series A

| Compound | n | Z | R₁(= R'₁) | R₂(= R'₂) | R₃(= R'₃) | MW |
|---|---|---|---|---|---|---|
| 1.0, 2HCl | 0 | —(CH$_2$)$_{12}$— | H | H | H | 327 |
| 1.1 | 0 | —(CH$_2$)$_{12}$— | H | H | CO$_2$CH$_3$ | 370 |
| 1.1, 2HCl | 0 | —(CH$_2$)$_{12}$— | H | H | CO$_2$CH$_3$ | 443 |
| 1.2 | 0 | —(CH$_2$)$_{12}$— | H | H | CO$_2$C$_2$H$_5$ | 398 |
| 1.3 | 0 | —(CH$_2$)$_{12}$— | H | H | CO$_2$nC$_4$H$_9$ | 454 |
| 1.4 | 0 | —(CH$_2$)$_{12}$— | H | H | CO$_2$isoC$_4$H$_9$ | 454 |
| 1.5 | 0 | —(CH$_2$)$_{12}$— | H | H | CO$_2$CH$_2$C$_6$H$_5$ | 522 |
| 1.6 | 0 | —(CH$_2$)$_{12}$— | H | H | CO$_2$CH$_2$pNO$_2$C$_6$H$_4$ | 612 |
| 1.7 | 0 | —(CH$_2$)$_{12}$— | H | H | CO$_2$C$_6$H$_5$ | 494 |
| 1.8 | 0 | —(CH$_2$)$_{12}$— | H | H | CO$_2$pFC$_6$H$_4$ | 530 |
| 1.8, 2HCl | 0 | —(CH$_2$)$_{12}$— | H | H | CO$_2$pFC$_6$H$_4$ | 603 |
| 1.9 | 0 | —(CH$_2$)$_{12}$— | H | H | CO$_2$pMeOC$_6$H$_4$ | 554 |
| 1.10 | 0 | —(CH$_2$)$_{12}$— | H | H | CO$_2$CH$_2$OCOCH$_3$ | 486 |
| 1.11 | 0 | —(CH$_2$)$_{12}$— | H | H | CO$_2$CH(CH$_3$)OCOCH$_3$ | 514 |
| 1.12 | 0 | —(CH$_2$)$_{12}$— | H | H | PO(OC$_6$H$_5$)$_2$ | 718 |
| 1.13 | 0 | —(CH$_2$)$_{12}$— | H | H | PO(OC$_2$H$_5$)$_2$ | 526 |
| 1.14 | 0 | —(CH$_2$)$_{12}$— | H | H | PO(ONa)$_2$ | 502 |
| 1.15 | 0 | —(CH$_2$)$_{12}$— | OH | H | H | 286 |
| 1.15, 2HCl | 0 | —(CH$_2$)$_{12}$— | OH | H | H | 359 |
| 1.16 | 0 | —(CH$_2$)$_{12}$— | OCH$_3$ | H | H | 314 |
| 1.17 | 0 | —(CH$_2$)$_{12}$— | OCOOCH$_2$CH$_3$ | H | H | 430 |
| 1.18 | 0 | —(CH$_2$)$_{12}$— | OCOOCH$_3$ | H | H | 402 |
| 1.19 | 0 | —(CH$_2$)$_{12}$— | OCOOC$_6$H$_5$ | H | H | 526 |
| 1.20 | 0 | —(CH$_2$)$_{12}$— | OCOSCH$_3$ | H | H | 434 |
| 1.21 | 0 | —(CH$_2$)$_{12}$— | OCOSCH$_2$CH$_3$ | H | H | 462 |
| 1.22 | 0 | —(CH$_2$)$_{12}$— | OCOCH$_3$ | H | H | 370 |
| 1.23 | 0 | —(CH$_2$)$_{12}$— | OCOC$_6$H$_5$ | H | H | 494 |
| 1.24 | 0 | —(CH$_2$)$_{12}$— | OCONHCH$_2$CH$_3$ | H | H | 428 |
| 1.25 | 0 | —(CH$_2$)$_{12}$— | OCONHC$_6$H$_5$ | H | H | 524 |
| 1.26 | 0 | —(CH$_2$)$_{12}$— | OPO(OCH$_2$CH$_3$)$_2$ | H | H | 558 |
| 1.27 | 0 | —(CH$_2$)$_{12}$— | —O—CO— | | H | 338 |
| 1.28 | 0 | —(CH$_2$)$_{12}$— | —O—SO— | | H | 378 |
| 1.29 | 0 | —(CH$_2$)$_{12}$— | —O—CS— | | H | 370 |
| 1.30 | 0 | —(CH$_2$)$_{12}$— | —S—CO— | | H | 370 |
| 1.31 | 0 | —(CH$_2$)$_{12}$— | —S—CS— | | H | 402 |
| 2.0, 2HCl | 0 | —(CH$_2$)$_{12}$— | H | —(CH$_2$)$_4$— | | 435 |
| 3.0 | 0 | —(CH$_2$)$_{12}$— | H | —(CH$_2$)$_5$— | | 390 |
| 4.0, 2HCl | 0 | —(CH$_2$)$_{12}$— | H | CH$_3$ | CH$_3$ | 383 |
| 5.0 | 0 | —(CH$_2$)$_{16}$— | H | H | H | 382 |
| 6.0 | 0 | —(CH$_2$)$_{12}$— | —(CH$_2$)$_2$— | | H | 306 |
| 6.1 | 0 | —(CH$_2$)$_{12}$— | —(CH$_2$)$_2$— | | CO$_2$CH$_3$ | 422 |
| 6.2 | 0 | —(CH$_2$)$_{12}$— | —(CH$_2$)$_2$— | | CO$_2$C$_2$H$_5$ | 450 |
| 6.3 | 0 | —(CH$_2$)$_{12}$— | —(CH$_2$)$_2$— | | CO$_2$nC$_4$H$_9$ | 506 |
| 6.4 | 0 | —(CH$_2$)$_{12}$— | —(CH$_2$)$_2$— | | CO$_2$isoC$_4$H$_9$ | 506 |
| 6.5 | 0 | —(CH$_2$)$_{12}$— | —(CH$_2$)$_2$— | | CO$_2$CH$_2$C$_6$H$_5$ | 574 |
| 6.6 | 0 | —(CH$_2$)$_{12}$— | —(CH$_2$)$_2$— | | CO$_2$CH$_2$pNO$_2$C$_6$H$_4$ | 664 |
| 6.7 | 0 | —(CH$_2$)$_{12}$— | —(CH$_2$)$_2$— | | CO$_2$C$_6$H$_5$ | 546 |
| 6.8 | 0 | —(CH$_2$)$_{12}$— | —(CH$_2$)$_2$— | | CO$_2$pFC$_6$H$_4$ | 582 |
| 6.8, 2HCl | 0 | —(CH$_2$)$_{12}$— | —(CH$_2$)$_2$— | | CO$_2$pFC$_6$H$_4$ | 655 |
| 6.9 | 0 | —(CH$_2$)$_{12}$— | —(CH$_2$)$_2$— | | CO$_2$pMeOC$_6$H$_4$ | 606 |
| 6.10 | 0 | —(CH$_2$)$_{12}$— | —(CH$_2$)$_2$— | | CO$_2$pNO$_2$C$_6$H$_4$ | 636 |
| 6.11 | 0 | —(CH$_2$)$_{12}$— | —(CH$_2$)$_2$— | | CO$_2$CH$_2$OCOCH$_3$ | 538 |
| 6.12 | 0 | —(CH$_2$)$_{12}$— | —(CH$_2$)$_2$— | | CO$_2$CH(CH$_3$)OCOCH$_3$ | 566 |
| 6.13 | 0 | —(CH$_2$)$_{12}$— | —(CH$_2$)$_2$— | | PO(OC$_6$H$_5$)$_2$ | 770 |
| 6.14 | 0 | —(CH$_2$)$_{12}$— | —(CH$_2$)$_2$— | | PO(OC$_2$H$_5$)$_2$ | 578 |
| 7.0, 2HCl | 0 | —(CH$_2$)$_{12}$— | —(CH$_2$)$_2$— | | CH$_3$ | 407 |
| 8.0, 2HCl | 0 | —(CH$_2$)$_{12}$— | —(CH$_2$)$_3$— | | H | 407 |
| 9.0, 2HCl | 0 | —(CH$_2$)$_{12}$— | —CH(CH$_3$)—CH$_2$— | | H | 407 |
| 10.0, 2HCl | 0 | —(CH$_2$)$_{12}$— | —C(CH$_3$)$_2$—CH$_2$— | | H | 435 |
| 11.0, 2HCl | 0 | —(CH$_2$)$_{12}$— |  | | H | 487 |
| 12.0, 2HBr | 1 | —(CH$_2$)$_{12}$— | H | H | H | 446 |
| 12.1 | 1 | —(CH$_2$)$_{12}$— | CO$_2$CH$_2$C$_6$H$_5$ | CO$_2$CH$_2$C$_6$H$_5$ | H | 820 |
| 12.2 | 1 | —(CH$_2$)$_{12}$— | CO$_2$C(CH$_3$)$_3$ | CO$_2$C(CH$_3$)$_3$ | H | 684 |

TABLE 1-continued

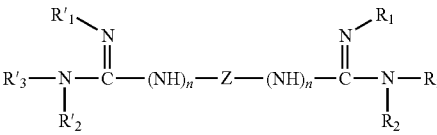

Series A

| Compound | n | Z | R₁(= R′₁) | R₂(= R′₂) | R₃(= R′₃) | MW |
|---|---|---|---|---|---|---|
| 13.0, 2HI | 1 | —(CH₂)₁₂— | H | CH₃ | CH₃ | 370 |
| 14.0, 2HCl | 1 | —(CH₂)₁₂— | C₆H₁₁ | C₆H₁₁ | H | 685 |
| 15.0, 2HBr | 1 | —(CH₂)₁₂— | —CH₂—CH₂— | | H | 500 |
| 16.0, 2HI | 1 | —(CH₂)₁₂— | —CH₂—CH₂—CH₂— | | H | 364 |
| 17.0, 2HI | 1 | —(CH₂)₁₂— | —CH₂—C(CH₃)₂—CH₂— | | H | 676 |

TABLE 2

| Compound | R_a | MW |
|---|---|---|
| 18.0 | H | 306 |
| 18.1 | CH₃ | 334 |
| 18.2 | CHF₂ | 406 |
| 18.3 | CHCl₂ | 472 |
| 18.4 | CF₃ | 442 |
| 18.5 | CCl₃ | 541 |
| 18.6 | C₆H₅ | 458 |
| 18.7 | CO₂C₂H₅ | 450 |
| 18.8 | CO₂H | 394 |
| 18.9 | CONH₂ | 392 |
| 18.10 | CN | 356 |
| 18.11 | CONHCH₃ | 420 |
| 18.12 | CON(CH₃)₂ | 448 |
| 18.13 | CONC₄H₈ | 500 |
| 18.14 | CONC₅H₁₀ | 528 |
| 18.15 | CONC₄H₈O | 532 |
| 18.16 | CONC₄H₈NH | 530 |
| 18.17 | CONC₄H₈NCH₃ | 558 |
| 18.18 | NH₂ | 336 |
| 18.19 | NHCH₃ | 364 |
| 18.20 | N(CH₃)₂ | 392 |
| 18.21 | NC₄H₈ | 444 |
| 18.22 | NC₅H₁₀ | 472 |
| 18.23 | NC₄H₈O | 476 |
| 18.24 | NC₄H₈NH | 474 |
| 18.25 | NC₄H₈NCH₃ | 502 |
| 18.26 | OCH₃ | 366 |
| 18.27 | OC₂H₅ | 394 |
| 18.28 | OCH₂C₆H₅ | 518 |
| 18.29 | CH₂NH₂ | 364 |
| 18.30 | CH2NHCH₃ | 392 |
| 18.31 | CH₂N(CH₃)₂ | 420 |
| 18.32 | CH₂NC₄H₈ | 472 |
| 18.33 | CH₂NC₅H₁₀ | 500 |
| 18.34 | CH₂NC₄H₈O | 504 |
| 18.35 | CH₂NC₄H₈NH | 502 |
| 18.36 | CH₂NC₄H₈NCH₃ | 530 |
| 18.37 | CH₂NHCOCH₃ | 448 |
| 18.38 | CH₂NHCOOCH₃ | 480 |
| 18.39 | CH₂NHCOOC₆H₅ | 604 |
| 18.40 | CH₂COOH | 422 |

TABLE 3

(IX)

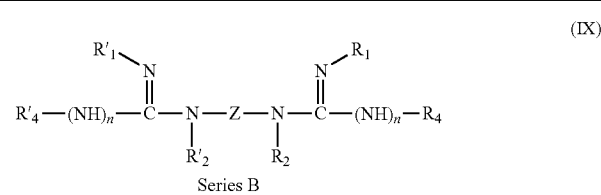

Series B

| Compound | n | Z | R₁(= R′₁) | R₄(= R′₄) | R₂(= R′₂) | MW |
|---|---|---|---|---|---|---|
| 20.0 | 0 | —(CH₂)₁₂— | H | CH₃ | H | 282 |
| 20.1 | 0 | —(CH₂)₁₂— | OH | CH₃ | H | 298 |
| 20.2 | 0 | —(CH₂)₁₂— | OCH₃ | CH₃ | H | 312 |
| 20.3 | 0 | —(CH₂)₁₂— | OCOOCH₂CH₃ | CH₃ | H | 370 |
| 20.4 | 0 | —(CH₂)₁₂— | OCOOCH₃ | CH₃ | H | 356 |
| 20.5 | 0 | —(CH₂)₁₂— | OCOOC₆H₅ | CH₃ | H | 418 |
| 20.6 | 0 | —(CH₂)₁₂— | OCOSCH₃ | CH₃ | H | 372 |
| 20.7 | 0 | —(CH₂)₁₂— | OCOSCH₂CH₃ | CH₃ | H | 386 |
| 20.8 | 0 | —(CH₂)₁₂— | OCOCH₃ | CH₃ | H | 340 |
| 20.9 | 0 | —(CH₂)₁₂— | OCOC₆H₅ | CH₃ | H | 402 |
| 20.10 | 0 | —(CH₂)₁₂— | OCONHCH₂CH₃ | CH₃ | H | 369 |
| 20.11 | 0 | —(CH₂)₁₂— | OCONHC₆H₅ | CH₃ | H | 417 |
| 20.12 | 0 | —(CH₂)₁₂— | OSO₂CH₃ | CH₃ | H | 470 |
| 20.13 | 0 | —(CH₂)₁₂— | OPO(OC₂H₅) | CH₃ | H | 586 |

TABLE 3-continued $$R'_4-(NH)_n-\underset{\underset{R'_2}{|}}{C}(=N-R'_1)-N-Z-N-\underset{\underset{R_2}{|}}{C}(=N-R_1)-(NH)_n-R_4 \quad (IX)$$

Series B

| Compound | n | Z | $R_1(=R'_1)$ | $R_4(=R'_4)$ | $R_2(=R'_2)$ | MW |
|---|---|---|---|---|---|---|
| 20.14 | | | 3-methyl-1,2,4-oxadiazol-5(4H)-one-N-(CH$_2$)$_{12}$-N-3-methyl-1,2,4-oxadiazol-5(4H)-one | | | 366 |
| 21.0 | 0 | —(CH$_2$)$_{12}$— | —(CH$_2$)$_3$— | | H | 334 |
| 22.0, 2HCl | 0 | —(CH$_2$)$_{12}$— | —(CH$_2$)$_4$— | | H | 435 |
| 23.0 | 0 | —(CH$_2$)$_{12}$— | —(CH$_2$)$_5$— | | H | 390 |
| 24.0 | 0 | —(CH$_2$)$_{12}$— | H | —(CH$_2$)$_3$— | | 334 |
| 25.0, 2TFA | | 4,4-dimethyl-tetrahydropyrimidin-2-yl-NH-(CH$_2$)$_{12}$-NH-3,4-dihydro-2H-pyrrol-5-yl | | | | 605 |
| 26.0 | 0 | —(CH$_2$)$_{12}$— | H | —CH$_2$OH | H | 298 |

The compounds according to the invention are presented if appropriate in the form of salts. As examples the hydrochlorides, citrates, tartrates, maleates, lactates, acetates and trifluoroacetates are mentioned.

According to the invention the carbamates and the N-phosphorylated derivatives of general formulae (V) and (VI) defined above can be obtained by a process characterized in that it comprises the reaction in diphasic medium of the bisamidine compounds of general formula (V) and (VI) in which $R_3$ and $R'_3$=H with a Cl—$R_3$ (or $R'_3$) derivative where $R_3$ and $R'_3$ are as defined above and different from H as illustrated in the examples.

The amidoxime derivatives of general formula (V) and (X) defined above can be obtained by a process characterized in that it comprises the reaction in basic medium of the bisamidoximes of general formulae (V) and (X) in which $R_1$ and $R'_1$=OH and an appropriate reagent as illustrated in the examples.

Advantageously, compounds of general formula (VI) group a2 and (VIII) group a4 defined above can be obtained by intramolecular cyclization of amidoxime or of amidoxime derivatives previously defined by general formula (V) group a1 in the presence of the appropriate reagent as illustrated in the examples.

Study of the activity of the products of the invention vis-à-vis parasites, and in particular *Plasmodium*, has shown that they present a strong activity in vitro.

Thus, the IC$_{50}$ values (50% inhibitory concentration of the parasite) are of the order of nM to µM vis-à-vis *P. falciparum*.

The invention therefore relates to the exploitation of the properties of the compounds for the production of pharmaceutical compositions.

The pharmaceutical compositions of the invention are characterized in that they contain an effective quantity of at least one compound as defined above, in combination with an inert pharmaceutical vehicle.

The invention also relates to the use of at least one of said compounds in order to produce medicaments for the treatment of infectious diseases, in particular malaria.

These compositions contain if appropriate active ingredients of other medicaments. Their combination with other antimalarial agents (such as lysosomotropic agents, atovaquone, antifolic or antifolinic agents, or artemisinin or one of its derivatives) for reasons of pharmacological synergy or avoidance of resistance is in particular mentioned.

They are also used advantageously in combination with compounds facilitating their assimilation.

The pharmaceutical compositions of the invention can be administered in different forms, more particularly by oral or injectable route or also by rectal route.

For administration by oral route, tablets, pills, gelatin capsules, drops are in particular available.

Other forms of administration include solutions which can be injected by intravenous, sub-cutaneous or intra-muscular route, produced from sterile or sterilizable solutions. These can also be suspensions or emulsions.

Suppositories can also be used for other forms of administration.

The compositions of the invention are particularly suitable for the treatment of infectious diseases in humans and animals, in particular malaria or babesioses.

By way of example, the dosage which can be used for humans corresponds to the following doses: for example 1 to 90 mg/kg are administered to the patient in one or more doses.

The invention also relates to the biological reagents containing the compounds defined above as active ingredients.

These reagents can be used as references or standards in studies of any anti-parasitic activities.

BRIEF DESCRIPTION OF THE DRAWIGNS

FIG. 1 represents the antimalarial activity of compound 6.0 as a function of the drug concentration, according to Desjardins' test, (Desjardins R. E. et al., Antimicrob. Agents Chemother. 1979, 16, 710-718).

Other characteristics and advantages of the invention will become apparent from the examples which follow, relative to the synthesis of the compounds and to the study of their anti-parasitic activity. In these examples, reference is made to FIG. 1, which represents the antimalarial activity of compound 6.0 as a function of the drug concentration, according to Desjardins' test, (Desjardins R. E. et al., Antimicrob. Agents Chemother. 1979, 16, 710-718).

EXAMPLE 1

Synthesis Intermediates

1,12-dicyanododecane

A suspension under vigorous stirring of 3.3 g (67.10 mmol) of sodium cyanide in 30 ml of dimethylsulphoxide is heated between 90 and 95° C. until completely dissolved. To the solution obtained and cooled down to a temperature below 50° C., 10 g (30.49 mmol) of 1,12 dibromododecane are added in very small portions and slowly. After stirring for 2 hours at ambient temperature, the suspension obtained is dissolved by adding 90 ml of dichloromethane and washed several times by a saturated aqueous solution of sodium chloride. After which, the organic phase, dried over sodium sulphate, is evaporated under reduced pressure. The cold oily residue taken up in ether, then evaporated to dryness, is crystallized and produces 6.44 g (96%) of white crystals.

Melting point: <40° C.
NMR $^1$H (CDCl$_3$, 100 MHz), δ (ppm): 1.24 (s, 16H); 1.60 (m, 4H); 2.31 (t, 4H)
FT-IR, ν (cm$^{-1}$): 2246 (CN)

Diethyltetradecanediimidoate dihydrochloride

Hydrochloric acid gas is bubbled through a solution cooled down to 0° C., of 20 ml of anhydrous ethanol, 60 ml of anhydrous ether and 5 g (22.73 mmol) of 1,12-dicyanododecane for 2 hours, then the reaction mixture is left under stirring overnight. After which, the solvents are evaporated off under reduced pressure. The solid residue obtained is crystallized and washed several times with ether then dried in a desiccator. 7.7 g (82%) of a white powder is obtained.

Melting point: 118-120° C.
NMR $^1$H (DMSO-d$_6$, 100 MHz), δ (ppm): 1.26 (s, 16H); 1.35 (t, 6H); 1.60 (m, 4H); 2.63 (t, 4H); 4.55 (q, 4H); 11.16 and 12.08 (2s, 4H)
FT-IR, ν (cm$^{-1}$): 1097 (C—O); 1651.50 (C=N); 3032 and 3118 (NH$_2$,Cl)

N,N'-di-benzyloxycarbonyl-S-methylisothiourea 2 ml (14.4 mol) of benzyl chloroformate are added dropwise, under vigorous stirring, to a solution of 1 g (3.60 mmol) of S-methylisothiourea sulphate in 40 ml of a diphasic mixture of dichloromethane/saturated aqueous sodium bicarbonate solution (1:1). Stirring is maintained at ambient temperature for 25 hours. After which, the aqueous phase is extracted 3 times with dichloromethane. The combined organic phases are then washed with water, then dried over sodium sulphate and evaporated under reduced pressure. The residue obtained is purified by chromatography on a silica column (DCM) in order to produce 1.06 g (82%) of product in the form of a yellow oil.

NMR $^1$H (CDCl$_3$, 100 MHz), δ (ppm): 2.46 (s, 3H); 5.24 (s, 4H); 7.42 (s, 10H); 11.91 (s, 1H)
FT-IR, ν (cm$^{-1}$): 1022 and 1173 (C—O); 1647 (C=N); 1751 (NCO); 3169 (NHCO)

N,N'-di-tert-butyloxycarbonyl-S-methylisothiourea

A saturated aqueous DCM/NaHCO$_3$ diphasic solution (100 ml) containing 5.81 g (26.60 mmol) of di-tert-butylcarbonate and 2.53 g (18.20 mmol) of S-methylisothiourea hemisulphate is left under vigorous stirring for 48 hours. After which, the separated aqueous phase, is extracted with 2×100 ml of DCM. The combined organic phases are then washed with 2×200 ml of water, then evaporated under reduced pressure. The residue is subsequently taken up in 100 ml of the saturated aqueous DCM/NaHCO$_3$ diphasic mixture to which 0.55 g (3.85 mmol) of S-methylisothiourea hemisulphate is added. The reaction mixture is again left under vigorous stirring for 72 hours. The combined organic phases, after the same treatment as previously, are dried over sodium sulphate and evaporated under reduced pressure. The residue is finally purified on silica (Hexane/CHCl$_3$ 5% then CHCl$_3$) in order to produce 3.46 g (90%) of product in the form of a white powder.

Melting point: 123-124° C.
NMR $^1$H (CDCl$_3$, 100 MHz), δ (ppm): 1.49 (s, 18H); 2.38 (s, 3H); 11.60 (s, 1H)
FT-IR, ν (cm$^{-1}$): 1043 and 1252 (C—O); 1667 (C=N); 1765 (NCO); 3337 (NHCO)

O-chloromethyl-S-ethyl carbonothioate

To a solution under stirring and cooled down between 0 and 5° C. of 44 ml (500 mmol) of chloromethyl chloroformate in 900 ml of ether, a solution of 37 ml (500 mmol) of ethanethiol and 69.3 ml (500 mmol) of triethylamine in 200 ml of ether is added dropwise over 2 hours. After which, the operating conditions are maintained for 30 minutes. The reaction mixture is then left under stirring for 16 hours at ambient temperature, then the precipitate formed is filtered and washed with ether. The combined ether phases are evaporated and the residue purified by distillation in order to produce 57 g (73%) of product in the form of a liquid.

Boiling point: 99-100° C./0.18 mbar
NMR $^1$H (CDCl$_3$, 100 MHz), δ (ppm):); 1.30 (t, 3H); 2.89 (q, 2H); 5.73 (s, 2H).
FT-IR, ν (cm$^{-1}$): 1719 (S—CO—O).

S-ethyl-O-iodomethyl carbonothioate 55 g (356 mmol) of O-chloromethyl-S-ethyl carbonothioate is added directly to a solution under stirring of 106.8 g (712 mmol) of sodium iodide and 3 g (35.6 mmol) of sodium bicarbonate in 450 ml of acetone. The reaction mixture is then left under stirring and at 40° C. for 4 hours. The precipitate formed is filtered and washed with acetone and ether. The organic phase is evaporated and the residue is divided between 1100 ml of hexane cooled down to 0° C. and 500 ml of cold water. The separated organic phase is then washed successively with 200 ml of 5% aqueous sodium bicarbonate, 200 ml of 1% aqueous sodium thiosulphate (until decolouration of the solution) and 2×200 ml of water. After drying of the hexane phase over sodium sulphate and evaporation under reduced pressure, 81 g (92%) of product is obtained in the form of yellowish liquid without purification.

NMR $^1$H (CDCl$_3$, 100 MHz), δ (ppm):); 1.30 (t, 3H); 2.89 (q, 2H,); 5.96 (s, 2H).
FT-IR, ν (cm$^{-1}$): 1715 (S—C—O).

O-acetyloxymethyl-S-ethyl carbonothioate

To a solution under stirring and cooled down to −20° C. of 26.7 g (325.2 mmol) of sodium acetate in 420 ml of anhydrous dimethylformamide, 80 g (325.2 mmol) of S-ethyl-O-iodomethyl carbonothioate is added dropwise over 2 hours. The reaction mixture is then left under stirring for 16 hours at ambient temperature, then the precipitate formed is filtered and washed with 20 ml of dimethylformamide and 40 ml of ether.

850 ml of ether and 350 ml of cold water are added to the organic phase in a separating funnel. The aqueous phase is isolated and extracted with 350 ml of water. The combined ether phases are then washed successively with 220 ml of 5% aqueous sodium bicarbonate, 220 ml of water, 2×220 ml of 0.01 N hydrochloric acid and 220 ml of water. After drying of the organic phase over sodium sulphate and evaporation, the residue is purified by distillation in order to produce 35 g (60%) of product in the form of yellowish liquid.

Boiling point: 82-83° C./.0.25 mbar

NMR $^1$H (CDCl$_3$, 100 MHz), δ (ppm): 1.30 (t, 3H); 2.09 (s, 3H); 2.87 (q, 2H); 5.76 (s, 2H).

FT-IR, ν (cm$^{-1}$): 1717 (S—CO—O); 1767 (CO—O).

Acetyloxymethyl chloroformate

To the solution of 33 g (185.4 mmol) of O-acetyloxymethyl-5-ethyl carbonothioate under stirring and cooled down between 0 and 5° C., 14.90 ml (185.4 mmol) of sulphuryl chloride is added. The operating conditions are maintained for 15 minutes then the reaction mixture is left under stirring for 45 minutes at ambient temperature. The S-ethyl chloride solution formed is evaporated at ambient temperature then at 20 mbar overnight. The residue obtained is then purified by distillation in order to produce 15.50 g (56%) of product in the form of orange liquid.

Boiling point: 75-76° C./0.17 mbar

NMR $^1$H (CDCl$_3$, 100 MHz), δ (ppm): 2.12 (s, 3H); 5.76 (s, 2H).

FT-IR, ν (cm$^{-1}$): 1724 (CO—O); 1773 (Cl—CO).

3,4-dihydro-5-methoxy-2H-pyrrole 23 ml (1 equivalent) of dimethylsulphate is added dropwise to the solution of 20.03 g (0.235 mol) of pyrrolidine-2-one in 85 ml of benzene, heated to 70° C. This reaction mixture is heated under reflux for 3 hours. After cooling down to ambient temperature, 19 ml of a 15N soda solution is added to the reaction mixture. The latter is poured into a separating funnel, and the aqueous phase is extracted 3 times with benzene. The combined organic phases are dried over sodium sulphate and evaporated under reduced pressure. The residue is distilled under vacuum in order to produce the product, a colourless liquid, with a yield of 58%.

Boiling point: 37° C. under 10$^{-2}$ mbar

NMR $^1$H (CDCl$_3$, 100 MHz), δ (ppm): 1.97 (m, 2H); 2.41 (t, 2H); 3.61 (t, 2H); 3.75 (s, 3H)

2-methylsulphanyl-3,4,5,6-tetrahydropyrimidinium iodide

The reaction mixture comprising one equivalent of 3,4,5,6-tetrahydro(1H)pyrimidine-2-thione and 1.2 equivalents of iodomethane in methanol (10 ml/g of thio-urea) is heated under reflux for 5 hours. After cooling down, the methanol is evaporated off under reduced pressure in order to quantitatively produce the product. The precipitate can then be washed in acetone or petroleum ether.

Melting point: 146-148° C.

NMR $^1$H (DMSO-d$_6$, 100 MHz): 1.94 (m, 2H); 2.66 (s, 3H); 3.44 (t, 4H); 9.53 (s, 2H) ppm.

5,5-Dimethyl-3,4,5,6-tetrahydro(1H)pyrimidine-2-thione 10 ml (167, 2 mmol; 2 eq.) of carbon disulphide is added to the solution of 10 ml (83.6 mmol) of 2,2-dimethyl-1,3-diaminopropane in 50 ml of absolute ethanol in a 250 ml flask. Then, 16.02 g (83.6 mmol) of EDC is added to the reaction mixture, which is stirred for 3 hours at ambient temperature. The ethanol is evaporated off, the residue is taken up in water and extracted with dichloromethane. After drying over Na$_2$SO$_4$ and evaporation of the organic phase, 11.2 g (93%) of product (white powder) is obtained, used without additional purification.

Melting point: 225-228° C.

NMR $^1$H (CDCl$_3$, 100 MHz): 0.91 (s, 6H); 2.88 (d, 4H); 7.46 (s, 2H) ppm.

5,5-dimethyl-2-methylsulphanyl-3,4,5,6-tetrahydropyrimidinium hydroiodide

The reaction mixture comprising one equivalent of 5,5-dimethyl-3,4,5,6-tetrahydro(1H)pyrimidine-2-thione and 1.2 equivalents of iodomethane in methanol (10 ml/g of thiourea) is heated under reflux for 5 hours. After cooling down, the methanol is evaporated off under reduced pressure in order to quantitatively produce the product. The precipitate can then be washed in acetone or petroleum ether.

.NMR $^1$H (CDCl$_3$, 100 MHz): 0.95 (s, 6H); 2.62 (s, 3H); 3.11 (s, 4H), 8.76 (s, 2H) ppm.

1-(N-tert-butyloxycarbonylamino)dodecane-12-ammonium hydrochloride

A solution of 4.02 g (18.4 mmol) of di-tert-butyldicarbonate in 60 ml of dioxane is added slowly, dropwise (over approximately two hours), to a solution of 15.01 g (75 mmol, 4.1 eq.) of 1,12-dodecanediamine in a dioxane/water (150/70 ml) mixture. The reaction mixture is stirred at ambient temperature for 24 hours, the excess of diamine is filtered out and the solvents are evaporated off under reduced pressure. The residue is taken up in a 1N HCl solution and dichloromethane. The precipitate formed in the aqueous phase is filtered out in order to produce the mono-Boc derivative and a little diamine, both in the form of the hydrochloride salt. This solid is recrystallized from ethanol and ether in order to produce 4.56 g (74% of yield) of mono-protected diamine salt, in the form of a white powder.

Melting point: 153-155° C.

NMR $^1$H (CD$_3$OD, 100 MHz), δ (ppm): 1.28 (m, 20H); 1.38 (s, 9H); 2.91 (m, 4H)

MS–FAB+: [M+H]$^+$: 301

[1-[N-(5,5-dimethyl-3,4,5,6-tetrahydropyrimidin-2-yl)amino]-12-(N'-tert-butyloxycarbonylamino)]dodecane hydroiodide 0.85 g (3 mmol) of 5,5-dimethyl-2-methylsulphanyl-3,4,5,6-tetrahydropyrimidinium iodide and 0.85 ml (2 eq.) of triethylamine are added to the suspension of 1.02 g (3 mmol) of 12-(N-tert-butyloxycarbonylamino)dodecane-1-ammonium chloride in 15 ml of acetonitrile. This reaction mixture is heated under reflux for 24 hours. After cooling down to ambient temperature, the amine which has not reacted is filtered out. The filtrate is evaporated off under reduced pressure and chromatographed on a silica column (eluent: $CH_2Cl_2$/$CH_3OH$/$NH_4OH$ 80:16:4) in order to produce 1.36 g (85%) of product.

NMR $^1H$ ($CD_3OD$, 100 MHz), δ (ppm): 1.07 (s, 6H); 1.37 (m, 29H); 3.05 (m, 8H).

1-[N-(5,5-dimethyl-3,4,5,6-tetrahydropyrimidin-2-yl)amino]dodecane-12-ammonium ditrifluoroacetate 1.06 g (2 mmol) of [1-[N-(5,5-dimethyl-3,4,5,6-tetrahydropyrimidin-2-yl)amino]-12-(N'-tert-butyloxycarbonylamino)]dodecane hydroiodide is solubilized in 15 ml of a TFA/$CH_2Cl_2$ (3/1) solution. This solution is stirred for 3 hours at ambient temperature; the excess trifluoroacetic acid is evaporated under reduced pressure in order to quantitatively produce 0.98 g of product.

NMR $^1H$ (DMSO-$d_6$, 100 MHz), δ (ppm): 1.0 (s, 6H); 1.3 (m, 20H); 3.0 (m, 8H); 8.0 (bs, 2H); 9.0 (s, 3H).

MS–ES$^+$: [M+H]$^+$: 311; [M+2H]$^{++}$/2: 156

Syntheses 1,12-bis(amidinyl)dodecane dihydrochloride: 1.0, 2HCl

Ammonia gas is bubbled for 2 hours through a solution, cooled down by an ice bath to a temperature below 10° C., of 45 ml of anhydrous ethanol and 5 g (13 mmol) of diethyltetradecanediimidoate hydrochloride. After which, the solvent is evaporated off under reduced pressure. The residue obtained is then washed several times with ether and dried in a desiccator. 3.53 g (83%) of product is obtained in the form of a white powder.

Melting point: 170-172° C.

NMR $^1H$ (DMSO-$d_6$, 100 MHz), δ (ppm): 1.25 (s, 16H); 1.58 (m, 4H); 2.37 (t, 4H); 8.82 (s, 4H); 9.10 (s, 4H)

FT-IR, ν (cm$^{-1}$): 1688 (C=N); 3081 (NH$_2$,Cl); 3245 (NH$_2$)

1,12-bis[N,N'-(methyloxycarbonyl)amidinyl]dodecane: 1.1

To a solution of 1 g (3.06 mmol of 1,12-bis(amidinyl) dodecane dihydrochloride in 60 ml of a dixane/water (3:1) mixture diphasic and cooled down by an ice bath, 60 ml (7.65 mmol) of methyl chloroformate, is added dropwise and under vigorous stirring, whilst maintaining the pH of the mixture between 10 and 12 with a 4N aqueous soda solution. The mixture is then left under stirring and at ambient temperature for 3 hours. After which, 100 ml of water is added. The precipitate formed is then separated, washed several times in water, then ether in order to produce, after drying in a desiccator, 1.30 g (77%) of product in the form of a white powder.

Melting point: 116-117° C.

NMR $^1H$ (DMSO-$d_6$, 100 MHz), δ (ppm): 1.69 (s, 16H); 1.96 (m, 4H); 2.61 (t, 4H); 3.97 (s, 6H); 9.06 (s, 4H).

FT-IR, ν (cm$^{-1}$): 1256 (C—O—C); 1633 (C=N); 1670 (NHCO); 3183 (NHCO); 3343 (NH)

MS–ES+: [M+H]$^+$: 371

1,12-bis[N,N'-(ethyloxycarbonyl)amidinyl]dodecane: 1.2

To a solution of 1 g (3.06 mmol) of 1,12-bis(amidinyl) dodecane dihydrochloride in 60 ml of a dioxane/water (3:1) diphasic mixture and cooled down by an ice bath, 0.73 ml (7.65 mmol) of ethyl chloroformate is added dropwise and under vigorous stirring, whilst maintaining the pH of the mixture between 10 and 12 with a 4N aqueous soda solution. The mixture is then left under stirring and at ambient temperature for 3 hours. After which, 100 ml of water is added. The precipitate formed is then separated, washed several times in water, then ether in order to produce, after drying in a desiccator, 0.98 g (80%) of product in the form of a white powder.

Melting point: 95-96° C.

NMR $^1H$ (DMSO-$d_6$, 100 MHz), δ (ppm): 1.63 (t, 6H); 1.71 (m, 16H); 1.93 (m, 4H); 2.63 (t, 4H); 4.49 (q, 4H); 8.95 and 9.12 (2s, 4H).

FT-IR, ν (cm$^{-1}$): 1251 (C—O—C); 1667 (C=N); 1757 (CO); 3186 (NHCO); 3330 (NH)

MS–ES+: [M+H]$^+$: 399; [M+2H]$^{2+}$/2: 200 (100%)

1,12-bis[N,N'-(butyloxycarbonyl)amidinyl]dodecane: 1.3

To a solution of 1 g (3.06 mmol) of 1,12-bis(amidinyl) dodecane dihydrochloride in 60 ml of a dioxane/water (3:1) diphasic mixture and cooled down by an ice bath, 0.99 ml (7.65 mmol) of ethyl chloroformate is added dropwise and under vigorous stirring, whilst maintaining the pH of the mixture between 10 and 12 with a 4N aqueous soda solution. The mixture is then left under stirring and at ambient temperature for 3 hours. After which, 100 ml of water is added. The precipitate formed is then separated, washed several times in water, then ether in order to produce, after drying in a desiccator, 1.12 g (80%) of product in the form of a white powder.

Melting point: 87-88° C.

NMR $^1H$ (CDCl$_3$, 100 MHz), δ (ppm): 0.88 (t, 6H); 1.21 (s, 16H) 1.48-1.70 (m, 8H); 1.88 (m, 4H); 2.24 (t, 4H); 4.03 (t, 4H); 6.21 (s, 2H); 9.24 (s, 2H).

FT-IR, ν (cm$^{-1}$): 1084 and 1234 (C—O—C); 1594 (C=N); 1660 (CO); 3313 (NHCO); 3441 (NH)

MS–ES+: [M+H]$^+$: 455

1,12-bis[N,N'-(isobutyloxycarbonyl)amidinyl]dodecane: 1.4

To a solution of 1 g (3.06 mmol) of 1,12-bis(amidinyl) dodecane dihydrochloride in 60 ml of a dioxane/water (3:1) diphasic mixture and which is cooled down by an ice bath, 1 ml (7.65 mmol) of isobutyl chloroformate is added dropwise and under vigorous stirring, whilst maintaining the pH of the mixture between 10 and 12 with a 4N aqueous soda solution. The mixture is then left under stirring and at ambient temperature for 3 hours. After which, 100 ml of water is added. The precipitate formed is then separated, washed several times in water, then ether in order to produce, after drying in a desiccator, 1.27 g (91%) of product in the form of a white powder.

Melting point: 102-103° C.

NMR $^1H$ (CDCl$_3$, 100 MHz), δ (ppm): 0.92 (d, 12H); 1.22 (s, 16H) 1.62 (m, 4H); 1.96 (m, 2H); 2.26 (t, 4H); 3.82 (d, 4H); 6.19 (s, 2H); 9.27 (s, 2H).

FT-IR, ν (cm$^{-1}$): 1069 and 1237 (C—O—C); 1599 (C=N); 1661 (CO); 3314 (NHCO); 3440 (NH)

MS–ES+: [M+H]$^+$: 455

1,12-bis[N,N'-(benzyloxycarbonyl)amidinyl]dodecane: 1.5

To a solution of 1 g (3.06 mmol) of 1,12-bis(amidinyl) dodecane dihydrochloride in 60 ml of a dioxane/water (3:1)

diphasic mixture and cooled down by an ice bath, 1.1 ml (7.65 mmol) of benzyl chloroformate is added dropwise under vigorous stirring, whilst maintaining the pH of the mixture between 10 and 12 with a 4N aqueous soda solution. The mixture is then left under stirring and at ambient temperature overnight. After which, 100 ml of water is added. The precipitate formed is then separated, washed several times in water, then ether in order to produce, after drying in a desiccator, 1.2 g (75%) of product in the form of a white powder.

Melting point: 118-119° C.

NMR $^1$H (DMSO-$d_6$, 100 MHz), δ (ppm): 1.19 (s, 16H); 1.47 (m, 4H); 2.13 (t, H); 4.96 (s, 4H); 7.30 (s, 10H); 8.29 (s, 2H); 8.50 (s, 2H).

FT-IR, ν (cm$^{-1}$): 693 and 745 (aromatic C—H); 1236 (C—O—C); 1648 (C=N); 1666 (CO); 3311 (NHCO); 3436 (NH)

MS–ES+: [M+H]$^+$: 523; [M+2H]$^{2+}$/2: 262 (100%)

1,12-bis[N,N'-(4-nitrobenzyloxycarbonyl)amidinyl]dodecane: 1.6

To a solution of 1 g (3.06 mmol) of 1,12-bis(amidinyl)dodecane dihydrochloride in 60 ml of a dioxane/water (3:1) diphasic mixture and cooled down by an ice bath, 1.65 g (7.65 mmol) of 4-nitrobenzyl chloroformate in solution in 5 ml of dioxane is added dropwise and under vigorous stirring. The pH of the solution is maintained between 10 and 12 with a 4N aqueous soda solution. The mixture is then left under stirring and at ambient temperature overnight. After which, 100 ml of water is added. The precipitate formed is then separated, washed several times in water, then ether in order to produce, after drying in a desiccator, 1.37 g (74%) of product in the form of a white powder.

Melting point: 87-88° C.

NMR $^1$H (DMSO-$d_6$, 100 MHz), δ (ppm): 1.22 (s, 16H); 1.51 (m, 4H); 2.18 (t, 4H); 5.15 (s, 4H); 7.59 (dd, 4H); 8.23 (dd, 4H); 8.69 (s, 4H).

FT-IR, ν (cm$^{-1}$): 1248 (C—O—C); 1344 and 1512 (NO$_2$); 1621 (C=N); 1658 (CO); 3316 (NHCO); 3406 (NH)

MS–ES+: [M+H]$^+$: 623

1,12-bis[N,N'-(phenyloxycarbonyl)amidinyl]dodecane: 1.7

To a solution of 1.5 g (4.59 mmol) of 1,12-bis(amidinyl)dodecane dihydrochloride in 80 ml of a dioxane/water (3:1) diphasic mixture and which is cooled down by an ice bath, 1.44 ml (11.47 mmol) of phenyl chloroformate is added dropwise under vigorous stirring, whilst maintaining the pH of the mixture between 10 and 12 with a 2N aqueous soda solution. The mixture is then left under stirring and at ambient temperature for 3 hours. After which, 150 ml of water is added and the solution extracted with 3×60 ml of DCM. The organic phase is then washed several times in water, then evaporated under reduced pressure. 1.77 g (78%) of product is obtained in liquid form.

NMR $^1$H (DMSO-$d_6$, 100 MHz), δ (ppm): 1.73 (s, 16H); 2.05 (m, 4H); 2.72 (t, 4H); 7.17-7.90 (m, 10H); 9.20 (s, 4H).

FT-IR, ν (cm$^{-1}$): 1623 (C=N); 1682 (COO); 3378 (NH and NHCO)

MS–ES+: [M+H]$^+$: 495

1,12-bis[N,N'-(4-fluorophenyloxycarbonyl)amidinyl]dodecane: 1.8

To a solution of 1.5 g (459 mmol) of 1,12-bis(amidinyl)dodecane dihydrochloride in 80 ml of a dioxane/water (3:1) diphasic mixture and cooled down by an ice bath, 1.50 ml (11.47 mmol) of 4-fluorophenyl chloroformate is added dropwise under vigorous stirring, whilst maintaining the pH of the mixture between 10 and 12 with a 2N aqueous soda solution. The mixture is then left under stirring and at ambient temperature for 3 hours. After which, 150 ml of water is added. The precipitate formed is then separated, washed several times in water, then ether in order to produce, after drying in a desiccator, 1.55 g (64%) of product in the form of a white powder.

NMR $^1$H (CDCl$_3$, 100 MHz), δ (ppm): 1.26 (s, 16H); 1.70 (m, 4H); 2.35 (t, 4H); 6.62-7.14 (m, 8H); 6.20 (s, 2H); 9.23 (s, 2H).

FT-IR, ν (cm$^{-1}$): 1177 (C—O—C); 1253 (C—F); 1622 (C=N); 1679 (COO); 3327 (NH and NHCO)

MS–ES+: [M+H]$^+$: 531

1,12-bis[N,N'-(4-fluorophenyloxycarbonyl)amidinyl]dodecane dihydrochloride: 1.8, 2HCl 1 g of 1.8 is added to 20 ml of an ethanolic solution saturated in hydrochloric acid gas. The reaction mixture, under vigorous stirring, is then heated to 50° C. for 2 hours. 150 ml of ether is added to the cold solution, then the mixture is left to rest in the refrigerator overnight. After decantation, the oily layer formed is taken up in 100 ml of distilled water, then filtered. The filtrate is finally lyophilized in order to produce the salt in the form of a white powder.

NMR $^1$H (DMSO-$d_6$, 100 MHz), δ (ppm): 1.75 (s, 16H); 2.15 (m, 4H); 3.06 (t, 4H); 7.20 (s, 2H); 7.70 and 7.78 (d, 8H); 7.85 and 8.21 (2s, 4H).

FT-IR, ν (cm$^{-1}$): 1684 (C=N); 1753 (NCO); 3324 (NH, HCl).

1,12-bis[N,N'-(4-methoxyphenyloxycarbonyl)amidinyl]dodecane: 1.9

To a solution of 1.5 g (4.59 mmol) of 1,12-bis(amidinyl)dodecane dihydrochloride in 80 ml of a dioxane/water (3:1) diphasic mixture and cooled down by an ice bath, 1.70 ml (11.47 mmol) of 4-methoxyphenyl chloroformate is added dropwise under vigorous stirring, whilst maintaining the pH of the mixture between 10 and 12 with a 2N aqueous soda solution. The mixture is then left under stirring and at ambient temperature for 3 hours. After which, 150 ml of water is added and the solution extracted with 3×60 ml of DCM. The organic phase is then washed several times in water, then evaporated under reduced pressure. 1.97 g (78%) of product is obtained in liquid form.

NMR $^1$H (CDCl$_3$, 100 MHz), δ (ppm): 1.21 (s, 16H); 1.62 (m, 4H); 2.28 (t, 4H); 3.73 (s, 6H); 6.71-7.06 (m, 8H); 6.18 (s, 2H); 9.21 (s, 2H).

FT-IR, ν (cm$^{-1}$): 1176 and 1189 (C—O—C); 1504 (aromatic C—H); 1623 (C=N); 1678 (COO); 3374 (NH and NHCO)

MS–ES+: [M+H]$^+$: 555

Diphenyl [1,12-bis(amidinyl)dodecane]-1,12-bis-N,N'-phosphonate: 1.12

To a solution of 1.5 g (4.59 mmol) of 1,12-bis(amidinyl)dodecane dihydrochloride in 30 ml of a dioxane./water (3:1) diphasic mixture and which is cooled down by an ice bath, 2.85 ml (13.76 mmol) of diphenylchlorophosphonate, is added dropwise and under vigorous stirring, whilst maintaining the pH of the mixture between 10 and 12 with a 4N aqueous soda solution. The mixture is then left under stirring and at ambient temperature for 3 hours. After which, 50 ml of water is added. The precipitate formed is then separated, washed several times in water, then ether in order to produce, after drying in a desiccator, 2.70 g (82%) of product in the form of a white powder.

Melting point: 100-101° C.
NMR $^1$H (DMSO-d$_6$, 100 MHz), δ (ppm): 1.65 (s, 16H); 1.93 (m, 4H); 2.79 (t, 4H); 7.68-7.81 (m, 20H); 8.31 (s, 2H); 8.71 (s, 2H)
NMR $^{31}$P (DMSO-d$_6$, 81 MHz), δ (ppm): −1.64
FT-IR, ν (cm$^{-1}$): 935 (P=O); 1230 (C—O); 1675 (C=N); 3169(NHPO); 3324 (N—H)
MS−FAB+: [M+H]$^+$: 719; [M+2H]$^{++}$/2: 360 (100%)

Diethyl [1,12-bis(amidinyl)dodecane]-1,12-bis-N,N'-phosphonate: 1.13

To a solution of 1 g (3.06 mmol) of 1,12-bis(amidinyl) dodecane dihydrochloride in 40 ml of a dioxane/water (3:1) diphasic mixture and which is cooled down by an ice bath, 1.11 ml (7.65 mmol) of diethylchlorophosphonate are is added dropwise under vigorous stirring, whilst maintaining the pH of the mixture between 10 and 12 with a 4N aqueous soda solution. The mixture is then left under stirring and at ambient temperature overnight. After which, the solution is extracted with dichloromethane (3×30 ml). The organic phase is then washed several times in water, then dried over sodium sulphate. Evaporation under reduced pressure of the solution produces an oily residue. The latter taken up in a minimum of ether and at −4° C. overnight, crystallizes in order to produce 1.08 g (67%) of product in the form of a white powder.

Melting point: 68-69° C.
NMR $^1$H (CDCl$_3$, 100 MHz), δ (ppm): 1.20 (s, 16H); 1.26 (t, 12H); 1.53 (m, 4H); 2.21 (t, 4H); 3.99 (quintuplet, 8H); 6.05 (s, 2H); 7.78 (s, 2H).
NMR $^{31}$P (CDCl$_3$, 81 MHz), δ (ppm): 8.76
FT-IR, ν (cm$^{-1}$): 793 and 1031 (P—O—CH$_2$CH$_3$); 958 (P=O); 1647 (C=N); 3187
(NHPO); 1581 and 3386 (N—H).
MS−ES+: [M+H]$^+$: 527

Sodium [1,12-bis(amidinyl)dodecane]-1,12-bis-N,N'-phosphonate: 1.14 a) [1,12-bis(amidinyl)dodecane]-1,12-bis-N,N'-phosphonic acid 1.36 ml (9.51 mmol) of trimethylsilane iodide is added dropwise to a solution of 10 ml of anhydrous dichloromethane cooled down to 0° C. under a nitrogen atmosphere and under stirring of 1 g (1.9 mmol) of 1.13. The operating conditions are thus maintained for 1 hour. The solution is then evaporated under reduced pressure. The cold residue is taken up in 10 ml of acetone containing 3 ml of water, then left under stirring for 24 hours. After which, the precipitate formed is separated, washed several times in acetone then recrystallized from ethanol in order to produce 0.52 g (66%) of product in the form of a white powder.

Melting point: 164-165° C.
NMR $^1$H (DMSO-d$_6$, 100 MHz), δ (ppm): 1.24 (s, 16H); 1.56 (m, 4H); 2.32 (t, 4H); 9.26 and 9.63 (2s, 8H).
NMR $^{31}$P (CDCl$_3$, 81 MHz), δ (ppm): −5.82
FT-IR, ν (cm$^{-1}$): 1044 and 1211 (P—OH); 939 (P=O); 1667 (C=N); 2324 (POH); 3019 (NHPO); 1557 and 3322 (N—H).
MS−ES+: [M+H]$^+$: 415 b) Sodium [1,12-bis(amidinyl)dodecane]-1,12-bis-N,N'-phosphonate: 1.14

A 0.1N soda solution (approximately 21 ml) is added dropwise to a suspension under stirring of 1 g of [1,12-bis(amidinyl)dodecane]-1,12-bis-N,N'-phosphonic acid in 20 ml of water until a pH of 7.4 is reached.

After which, the solution is lyophilized in order to produce a white powder.

NMR $^{31}$P (81 MHz), δ(ppm): −3.16

1,12-bis(N,N'-hydroxyamidinyl)dodecane: 1.15

13.70 g (196.91 mmol) of hydroxylamine hydrochloride is added to a hydro-alcoholic soda solution [prepared from 8.22 g of soda, 36 ml of water and 138 ml of 95% ethyl alcohol]. After stirring for 15 minutes, 20 g (90.91 mmol) of 1,12-dicyanododecane is added. The reaction mixture is then heated under reflux for 72 hours then evaporated under reduced pressure. The residue obtained is subsequently taken up in water and left under stirring, then filtered. The precipitate is separated and washed several times in water and petroleum ether. After recrystallization from ethanol and drying in a desiccator overnight, 25 g (96%) of product is obtained in the form of a white powder.

Melting point: 170-171° C.
NMR $^1$H (DMSO-d$_6$, 100 MHz), δ (ppm): 1.70 (s, 16H); 1.90 (m, 4H); 2.39 (t, 4H); 5.75 (s, 4H); 9.13 (s, 2H).
FT-IR, ν (cm$^{-1}$): 1661 (C=N); 3244 (N—OH); 3315 and 3400 (NH$_2$)
+TOF MS: 287 (M+H); 254 (M−32); 144 (M+H/2)

1,12-bis(N,N'-methoxyamidinyl)dodecane: 1.16

1.70 ml (17.48 mmol) of dimethylsulphate is added dropwise to a suspension cooled down by an ice bath and under stirring of 2 g (7 mmol) of 1.15 in 50 ml of a dioxane/NaOH 0.7 N diphasic mixture. Stirring is maintained overnight at ambient temperature. The reaction mixture is then extracted with DCM, filtered and the filtrate washed with 3×100 ml of water. The organic phase is dried over sodium sulphate and evaporated under reduced pressure. The cold residue crystallizes by the addition of petroleum ether and, after drying in a desiccator, produces 1.05 g (48%) of product in the form of a white powder.

Melting point: 85-86° C.
NMR $^1$H (CDCl$_3$, 100 MHz), δ (ppm): 1.23 (s, 16H); 1.50 (m, 4H); 2.10 (t, 4H); 3.74 (s, 6H). 4.44 (s, 4H).
FT-IR, ν (cm$^{-1}$): 1048 (N—O—C); 1643 (C=N); 3288 and 3433 (NH$_2$)
+TOF MS: 315 (M+H)

1,12-bis(N,N'-ethoxycarbonyloxyamidinyl)dodecane: 1.17

1.40 ml (14.68 mmol) of ethyl chloroformate in 5 ml of chloroform is added dropwise to a suspension under stirring of 2 g (7 mmol) of 1.15 and 2.65 ml of triethylamine (18.9 mmol) in 45 ml of chloroform. Stirring is maintained for 3 hours at ambient temperature. The reaction mixture is then filtered and the filtrate washed with 3×100 ml of water. The organic phase is dried over sodium sulphate and evaporated under reduced pressure. After crystallization of the cold residue, the crystals are washed in petroleum ether and dried in a desiccator in order to produce 2.53 g (84.33%) of product in the form of a white powder.

Melting point: 100-101° C.

NMR $^1$H (CDCl$_3$, 100 MHz), δ (ppm): 1.21 (s, 16H); 1.29 (t, 6H) 1.53 (m, 4H); 2.19 (t, 4H); 4.23 (quartet, 4H). 4.79 (s, 4H).

FT-IR, ν (cm$^{-1}$): 1240 (C—O—C); 1620 (C=N); 1741 (OCOO); 3374 and 3508 (NH$_2$)

+TOF MS: 431 (M+H)

1,12-bis(N,N'-methoxycarbonyloxyamidinyl)dodecane: 1.18

1.14 ml (14.68 mmol) of methyl chloroformate in 5 ml of chloroform is added dropwise to a suspension under stirring of 2 g (7 mmol) of 1.15 and 2.65 ml of triethylamine (18.9 mmol) in 45 ml of chloroform. Stirring is maintained for 3 hours at ambient temperature. The reaction mixture is then filtered and the filtrate washed with 3×100 ml of water. The organic phase is dried over sodium sulphate and evaporated under reduced pressure. The cold residue is washed with petroleum ether then separated and dried in a desiccator in order to produce 2.05 g (73%) of product in the form of a white powder.

Melting point: 79-80° C.

NMR $^1$H (CDCl$_3$, 100 MHz), δ (ppm): 1.21 (s, 16H); 1.53 (m, 4H); 2.19 (t, 4H); 3.81 (s, 6H). 4.81 (s, 4H).

FT-IR, ν (cm$^{-1}$): 1247 (C—O—C); 1622 (C=N); 1750 (OCOO); 3380 and 3497 (NH$_2$)

+TOF MS: 403 (M+H)

1,12-bis(N,N'-phenoxycarbonyloxyamidinyl)dodecane: 1.19

To a suspension under stirring of 2 g (7 mmol) of 1.15 and 2.65 of triethylamine (18.9 mmol) in 30 ml DMF and cooled down by cold water bath, 1.85 ml (14.68 mmol) of phenyl chloroformate is added dropwise. Stirring is maintained for 4 hours at ambient temperature then the reaction mixture is filtered and the filtrate diluted with 150 ml of ethyl acetate. The solution is then washed with water (100 ml) and with a saturated sodium chloride solution (2×100 ml). The organic phase is dried over sodium sulphate and evaporated under reduced pressure. The cold residue is washed with petroleum ether then separated and dried in a desiccator in order to produce 3.02 g (82%) of product in the form of a white powder.

Melting point: 108-109 C.

NMR $^1$H (DMSO-d$_6$, 100 MHz), δ (ppm): 1.72 (s, 16H); 1.98 (m, 4H); 2.52 (t, 4H); 6.98 (s, 4H); 7.65-7.98 (m, 10H).

FT-IR, ν (cm$^{-1}$): 1197 and 1241 (C—O—C); 1633 (C=N); 1770(OCOO); 3309 and 3473 (NH$_2$)

+TOF MS: (M+H)

1,12-bis(N,N'-thiomethylcarbonyloxyamidinyl)dodecane: 1.20

1.55 ml (18.06 mmol) of thiomethyl chloroformate in 5 ml of chloroform is added dropwise to a suspension under stirring of 2.46 g (8.60 mmol) of 1.15 and 3.26 ml of triethylamine (23.22 mmol) in 45 ml of chloroform. Stirring is maintained for 2 hours at ambient temperature. The reaction mixture is then filtered and the filtrate washed with 3×100 ml of water. The organic phase is dried over sodium sulphate and evaporated under reduced pressure. The cold residue is washed with petroleum ether then separated and dried in a desiccator in order to produce 3.45 g (92%) of product in the form of a white powder.

Melting point: 89-90° C.

NMR $^1$H (CDCl$_3$, 100 MHz), δ (ppm): 1.24 (s, 16H); 1.56 (m, 4H); 2.20 (t, 4H); 2.31 (s, 6H). 4.79 (s, 4H).

FT-IR, n (cm$^{-1}$): 1131 (C—O—C); 1605 (C=N); 1719 (OCOS); 3384 and 3496 (NH$_2$)

ES+MS: 435 (M+H)

1,12-bis(N,N'-thioethylcarbonyloxyamidinyl)dodecane: 1.21

1.53 ml (14.68 mmol) of thioethyl chloroformate in 5 ml of chloroform is added dropwise to a suspension under stirring of 2 g (7 mmol) of 1.15 and 2.65 ml of triethylamine (18.9 mmol) in 45 ml of chloroform. Stirring is maintained for 3 hours at ambient temperature. The reaction mixture is then filtered and the filtrate washed with 3×100 ml of water. The organic phase is dried over sodium sulphate and evaporated under reduced pressure. The cold residue is washed with petroleum ether then separated and dried in a desiccator in order to produce 2.70 g (83%) of product in the form of a white powder.

Melting point: 59-60° C.

NMR $^1$H (CDCl$_3$, 100 MHz), δ (ppm): 1.23 (s, 16H); 1.30 (t, 6H) 1.56 (m, 4H); 2.20 (t, 4H); 2.86 (quartet, 4H). 4.80 (s, 4H).

FT-IR, n (cm$^{-1}$): 1127 (C—O—C); 1608 (C=N); 1718 (OCOS); 3386 and 3496 (NH$_2$)

ES+MS: 462 (M+H)

1,12-bis(N,N'-acetoxyamidinyl)dodecane: 1.22

To 26 ml (280 mmol) of acetic anhydride under stirring and which has been cooled down by an iced water bath, 2 g (7 mmol) of 1,15 is added portion by portion. Stirring is maintained for 2 hours at ambient temperature. 100 ml of chloroform is added to the reaction mixture. The solution is then washed successively with 2×100 ml of a saturated aqueous solution of sodium chloride, 3×100 ml of a 3N soda solution and 100 ml of water. The organic phase is dried over sodium sulphate and evaporated under reduced pressure. After crystallization of the cold residue, the crystals are washed in petroleum ether and dried in a desiccator in order to produce 2.33 g (90%) of product in the form of a white powder.

Melting point: 128-129° C.

NMR $^1$H (CDCl$_3$, 100 MHz), δ (ppm): 1.23 (s, 16H); 1.55 (m, 4H); 2.12 (s, 6H); 2.23 (t, 4H); 5.74 (s, 4H).

FT-IR, ν (cm$^{-1}$): 1232 (C—O—C); 1633 (C=N); 1736 (OCO); 3319 and 3425 (NH$_2$)

+TOF MS: 371 (M+H)

1,12-bis(N,N'-benzoyloxyamidinyl)dodecane: 1.23

To a suspension under stirring of 1.5 g (5.24 mmol) of 1.15 and 2 ml of triethylamine (14.16 mmol) in 30 ml of DMF and which has been cooled down by a cold water bath, 1.28 ml (14.68 mmol) of benzoyl chloride is added dropwise. Stirring is maintained for 3 hours at ambient temperature, then the reaction mixture is filtered and the filtrate precipitated in 200 ml of cold water. The precipitate is then separated, washed in water and petroleum ether then dried in a desiccator in order to produce 2.25 g (87%) of product in the form of a white powder.

Melting point: 158-159 C.

NMR $^1$H (DMSO-d$_6$, 100 MHz), δ (ppm): 1.73 (s, 16H); 2.01 (m, 4H); 2.56 (t, 4H); 6.94 (s, 4H); 7.96-8.11 (m, 6H); 8.54-8.61 (m, 4H).

FT-IR, ν (cm$^{-1}$): 684 and 699 (aromatic C—Hs); 1266 (C—O—C); 1625 (C=N); 1721 (OCO); 3315 and 3452 (NH$_2$)

1,12-bis(N,N'-ethylcarbamoyloxyamidinyl)dodecane: 1.24

1.16 ml (14.68 mmol) of ethyl isocyanate is added dropwise to a suspension under stirring of 2 g (7 mmol) of 1.15 and 1.01 g of potassium carbonate (7.34 mmol) in 80 ml of chloroform. Stirring is maintained overnight at ambient temperature. The reaction mixture is then filtered and the filtrate washed with 2×100 ml of water. The organic phase is subsequently dried over sodium sulphate and evaporated under reduced pressure in order to produce 2.22 g (74%) of product in the form of coloured oil.

NMR $^1$H (CDCl$_3$, 100 MHz), δ (ppm): 1.14 (t, 6H); 1.22 (s, 16H); 1.51 (m, 4H); 2.12 (t, 4H); 3.26 (quintuplet, 4H). 5.00 (s, 4H); 6.44 (t, 2H).

FT-IR, ν (cm$^{-1}$): 1650 (C=N); 1701 (OCONH); 3335 (NH); 3374 and 3490 (NH$_2$)

+TOF MS: 429 (M+H)

1,12-bis(N,N'-phenylcarbamoyloxyamidinyl)dodecane: 1.25

To a suspension under stirring cooled down to 0° C. by a cold water bath of 2 g (7 mmol) of 1.15 and 1.01 g of potassium carbonate (7.34 mmol) in 40 ml of DMF 1.6 ml (14.68 mmol) of phenyl isocyanate is added dropwise. Stirring is maintained for 2 hours 30 minutes at ambient temperature. The reaction mixture is then filtered and the filtrate precipitated in 150 ml of cold water. The precipitate is subsequently washed successively with water, acetone and ether. After drying in a desiccator, 2.95 g (80%) of product are obtained in the form of a white powder.

Melting point: 134-135° C.

NMR $^1$H (DMSO-d$_6$, 100 MHz), δ (ppm): 1.72 (s, 16H); 2.0 (m, 4H); 2.55 (t, 4H); 6.83 (s, 4H); 7.54 (t, 2H); 7.76 (t, 4H); 7.93 (t, 4H); 9.65 (s, 2H).

FT-IR, ν (cm$^{-1}$): 1018 and 1220 (C—O—C); 1628 (C=N); 1708 (CON); 3249 (OCONH); 3345 and 3455 (NH$_2$)

ES+MS: 525 (M+H); 263 (M+H/2)

Diethyl [1,12-bis(amidinyl)dodecane]-1,12-bis-N,N'-phosphate: 1.26

To a suspension under stirring cooled down to 0° C. by a cold water bath of 2 g (7 mmol) of 1.15 and 2.06 ml of triethylamine (14.68 mmol) in 30 ml of DMF, 2.08 ml (14.33 mmol) of diethylchlorophosphonate is added dropwise. Stirring is maintained for 16 hours at ambient temperature. The reaction mixture is then filtered and the filtrate taken up in 150 ml of ethyl acetate. The organic phase is subsequently washed with 3×200 ml of water, then dried over sodium sulphate and evaporated under reduced pressure in order to produce 2.88 g (74%) of product in the form of coloured oil.

NMR $^1$H (CDCl$_3$, 100 MHz), δ (ppm): 1.21 (s, 16H); 1.31 (t, 12H); 1.51 (m, 4H); 2.15 (t, 4H); 4.15 (quintuplet, 8H); 4.30 (s, 4H).

FT-IR, ν (cm$^{-1}$): 837 and 1027 (OP—O—CH$_2$CH$_3$); 969 (OP=O); 1648 (C=N); 3323 and 3487 (NH$_2$).

ES+MS: 559 (M+H)

1,12-bis[(1,2,4-oxadiazol-5(4H)-one)-3-yl]dodecane: 1.27

A suspension, under stirring, of 4 g (9.30 mmol) of 1.17 in 70 ml of xylene, is heated to 150° C. for 2 hours (until a coloured oily layer is formed). The reaction mixture is then evaporated under reduced pressure. The solid residue obtained is subsequently dissolved in 50 ml of DMSO then precipitated in 200 ml of cold water. The precipitate formed is separated then redissolved in acetone and filtered out. The filtrate, dried over sodium sulphate and evaporated under reduced pressure, after drying in a desiccator, produces 2.97 g (94%) of product in the form of coloured crystals.

Melting point: 150-151° C.

NMR $^1$H (DMSO-d$_6$, 100 MHz), δ (ppm): 1.71 (s, 16H); 2.03 (m, 4H); 2.93 (t, 4H).

FT-IR, n (cm$^{-1}$): 1718 (C=N); 1783 (OCONH); 3163 (NHCO).

ES+MS: 339 (M+H)

1,12-bis[(1,2,3,5-oxathiadiazol-2(3H)-oxide)-4-yl]dodecane: 1.28

There is added dropwise to a suspension under stirring of 2 g (7 mmol) of 1.15 and 2.82 ml of pyridine (34.96 mmol) in 30 ml of DMF which has been cooled down to 0° C., 1.1 ml (15.03 mmol) of thionyl chloride. Stirring is maintained for 45 minutes in the cold state, then the reaction solution is precipitated in 150 ml of cold water. The precipitate, filtered and dried in a desiccator, produces 1.65 g (62%) of product in the form of coloured powder.

Melting point: 94-95° C.

NMR $^1$H (DMSO-d$_6$, 100 MHz), δ (ppm): 1.71 (s, 16H); 2.05 (m, 4H); 2.99 (t, 4H).

FT-IR, n (cm$^{-1}$): 1146 (NSOC); 1615 (C—N); 1655 (C=N); 3219 and 3323 (NHSO).

ES+MS: 379 (M+H)

1,12-bis[(1,2,4-oxadiazol-5(4H)-thione)-3-yl]dodecane: 1.29

There is added slowly to a suspension under stirring of 2 g (5.4 mmol) of 1.22 and 2.5 ml (34.96 mmol) of carbon sulphide in 50 ml of DMF which has been cooled down to 0° C., 1.32 g (32.97 mmol) of 60% sodium hydride. Stirring is maintained for 45 minutes in the cold state, then for 2 hours at ambient temperature. The reaction solution is then precipitated in 150 ml of cold water, acidified to pH 5 with 2N HCl, then extracted with 3×50 ml of ethyl acetate. The organic phase washed in water, then dried over sodium sulphate and evaporated under reduced pressure produces a solid residue. The latter is then washed with ether in order to produce, after drying in a desiccator, 1.45 g (72%) of product in the form of coloured powder.

NMR $^1$H (DMSO-d$_6$, 100 MHz), δ (ppm): 1.71 (s, 16H); 2.06 (m, 4H); 3.02 (t, 4H); 9.25 (s, 2H)

FT-IR, ν (cm$^{-1}$): 1644 (C=N); 1737 (SCONH); 3090 (NHCO).

ES+MS: 371 (M+H); 313 [M+2H−60 (SCO)]

1,12-bis[(1,2,4-thiadiazol-5(4H)-one)-3-yl]dodecane: 1.30

A suspension of 2 g (7 mmol) of 1.15 and 3.74 g (21 mmol) of 1,1'-thiocarbonyl diimidazole in 70 ml of THF is left under stirring and at ambient temperature for 16 hours. The reaction mixture is diluted with 150 ml of water and extracted with 3×70 ml of ethyl acetate. The organic phase is then washed with water, dried over sodium sulphate and evaporated under reduced pressure. The oily residue is taken up in 50 ml of THF, to which 5.32 ml (41.96 mmol) of $BF_3$, $Et_2O$ is added. The reaction mixture obtained is subsequently left under stirring overnight at ambient temperature. The solution is diluted with water, extracted with ethyl acetate, washed in water, dried, then evaporated under reduced pressure. The cold residue obtained is then taken up in 50 ml of ethanol and precipitated in 200 ml of cold water. The isolated precipitate is finally washed in water and dried in order to produce 1.62 g (62.55%) of product in the form of orange powder.

NMR $^1H$ (DMSO-$d_6$, 100 MHz), δ (ppm): 1.70 (s, 16H); 2.04 (m, 4H); 2.93 (t, 4H); 9.30 (s, 2H)

FT-IR, ν ($cm^{-1}$): 1666 (C=N); 1707 (SCONH); 3129 (NHCO).

+TOF MS: 313 [M+2H−60 (SCO)]

1,14-di(pyrrolidin-1-yl)tetradecane-1,14-diimine: 2.0, 2HCl

A mixture constituted by 1.16 g (3 mmol) of diethyl tetradecanediimidoate dihydrochloride, 0.51 ml of pyrrolidine and 15 ml of ethanol is heated under reflux for 24 hours. After evaporation, the residue obtained is recrystallized from a methanol-ether mixture in order to produce 0.97 g (75%) of beige powder.

Melting point: 171° C.

NMR $^1H$ (CD$_3$OD, 250 MHz), δ (ppm): 1.35 (m, 16H); 1.68 (m, 4H); 2.08 (m, 8H); 2.55 (t, 4H); 3.42 (t, 4H); 3.70 (t, 4H); 9.12 (s, 4H)

1,14-di(piperidin-1-yl)tetradecane-1,14-diimine: 3.0

1.68 ml (20 mmol) of anhydrous piperidine is added to 2.2 g (10 mmol) of 1,12-dicyanododecane and 1.98 g (20 mmol) of CuCl. The mixture, initially green, turns blue. It is then heated at 80° C. for 20 hours, and the resultant red solution is poured into 125 ml of ether and stirred for 2 minutes with 12 ml of NaOH (30% aqueous). The organic phase is isolated and dried over $SO_4Na_2$, filtered and evaporated. The residue obtained is recrystallized from ether (yield 50%).

Melting point: 149-150° C.

NMR $^1H$ (CDCl$_3$, 100 MHz), δ (ppm): 1.3 (m, 20H); 1.4-1.6 (m, 12H); 2.2 (t, 4H); 3.3 (m, 8H); 6.5 (m, 2H).

$N^1,N^1,N^{14},N^{14}$-tetramethyltetradecanediimidamide: 4.0, 2HCl 1.16 g (3 mmol) of diethyl tetradecanediimidoate dihydrochloride and 1.1 ml of a solution of dimethylamine in ethanol (5.6M) are mixed with 15 ml of ethanol and heated under reflux for 26 hours. After which, the solvent is evaporated off and the residue obtained is recrystallized from a methanol-ether mixture in order to produce 0.98 g (85%) of greenish powder.

Melting point: 209° C.

NMR $^1H$ (CD$_3$OD, 250 MHz), δ (ppm): 1.35 (m, 16H); 1.68 (m, 4H); 2.59 (t, 4H); 3.12 (s, 6H); 3.25 (s, 6H); 9.10 (s, 4H)

$N^1,N^1,N^{14},N^{14}$-tetramethyloctadecanediimidamide: 5.0

A mixture of 0.46 g (1.2 mmol) of diethyl octadecanediimidoate dihydrochloride in 5.3 ml of a solution of ammonia in methanol (2M) is cooled down to −10° C. for 1 hour, then left at ambient temperature for 15 hours. After evaporation of the solvent, the residue obtained is recrystallized using a methanol-ether mixture, filtered and dried in a desiccator, in order to produce 0.25 g (54%) of product.

Melting point: 196-198° C.

NMR $^1H$ (DMSO-$d_6$, 250 MHz), δ (ppm): 1.24 (m, 24H); 1.60 (m, 4H); 2.37 (t, 4H); 8.82 (s, 4H); 9.10 (s, 4H)

1,12-bis(imidazolin-2-yl)dodecane: 6.0 a) 1,12-bis(imidazolin-2-yl)dodecane dihydrochloride: 6.0, 2HCl 1.64 ml (24.55 mmol) of ethylene diamine are added slowly and in the cold state to a solution of 4.5 g (11.69 mmol) of 1,14-diethoxytetradecane-1,14-diimine hydrochloride in 100 ml of absolute ethanol. The reaction mixture is then heated under reflux for 4 hours. After evaporation under reduced pressure with a minimum of solvent, the cold residue obtained is crystallized by the addition of ether under stirring. The precipitate, isolated by filtration, is then washed in ether and dried in a desiccator, in order to produce 3.9 g (88%) of product in the form of a white powder.

Melting point: 191-192° C.

NMR $^1H$ (DMSO-$d_6$, 100 MHz), δ (ppm): 1.22 (s, 16H); 1.57 (m, 4H); 2.45 (t, 4H); 3.75 (s, 8H); 9.28 (s, 4H).

FT-IR, ν ($cm^{-1}$): 1600 (C=N); 3031 (C=NH, HCl); 3200 (N—H)

b) 1,12-bis(imidazolin-2-yl)dodecane: 6.0

Triethylamine is added dropwise and under stirring to an aqueous solution (20 ml) of 2 g (5.28 mmol) of 6.0, 2 HCl, until a pH of 14 is reached. The precipitate formed is separated, washed in water, acetone, then ether and dried in a desiccator in order to produce 1.4 g (86.4%) of free base in the form of a white powder. This powder is then recrystallized from methanol and produces 1.26 g (90%) of product in the form of white crystals.

Melting point: 176-178° C.

NMR $^1H$ (CD$_3$OD, 100 MHz), δ (ppm): 1.29 (s, 16H); 1.55 (m, 4H); 2.20 (t, 4H); 3.52 (s, 8H).

FT-IR, ν ($cm^{-1}$): 1611 (C=N); 3177 (N—H)

1,12-bis[N,N'-(methyloxycarbonyl)imidazolin-2-yl] dodecane: 6.1

0.80 ml (10.29 mmol) of methyl chloroformate in solution in 5 ml of chloroform is added dropwise and under stirring to a suspension of 1.5 g (4.90 mmol) of 1,12-bis(imidazolin-2-yl)dodecane and 1.5 ml (10.78 mmol) of triethylamine in 25 ml of chloroform cooled down by an ice bath. After which, stirring is maintained at ambient temperature overnight. The reaction mixture is then filtered and the filtrate washed successively with 120 ml of water, 120 ml of a saturated aqueous solution of sodium chloride and 2×120 ml of water. After drying over sodium sulphate, the organic phase is evaporated under reduced pressure in order to produce an oily residue. The latter, taken up in petroleum ether and left at −4° C. produces 1.51 g (73%) of product in the form of a white liquid.

NMR $^1H$ (CDCl$_3$, 100 MHz), δ (ppm): 1.20 (s, 16H); 1.58 (m, 4H); 2.64 (t, 4H); 3.70 (s, 8H); 3.76 (s, 6H).

FT-IR, ν ($cm^{-1}$): 1142 and 1194 (C—O—C); 1642 (C=N); 1723 (NCO).

1,12-bis[N,N'-(ethyloxycarbonyl)imidazolin-2-yl]dodecane: 6.2

0.98 ml (10.29 mmol) of ethyl chloroformate in solution in 5 ml of chloroform is added dropwise and under stirring to a suspension of 1.5 g (4.90 mmol) of 1,12-bis(imidazolin-2-yl)dodecane and 1.5 ml (10.78 mmol) of triethylamine in 25 ml of chloroform cooled down by an ice bath. After which, stirring is maintained at ambient temperature overnight. The reaction mixture is then filtered and the filtrate washed successively with 120 ml of water, 120 ml of a saturated aqueous solution of sodium chloride and 2×120 ml of water. After drying over sodium sulphate, the organic phase is evaporated under reduced pressure in order to produce 1.78 g (81%) of product in the form of an oil.

NMR $^1$H (CDCl$_3$, 100 MHz), δ (ppm): 1.22 (s, 16H); 1.30 (t, 6H); 1.59 (m, 4H); 2.65 (t, 4H); 3.72 (s, 8H); 4.16 (q, 4H).

FT-IR, ν (cm$^{-1}$): 1073 and 1099 (C—O—C); 1644 (C=N); 1720 (NCO).

1,12-bis[N,N'-(butyloxycarbonyl)imidazolin-2-yl]dodecane: 6.3

1.33 ml (10.29 mmol) of butyl chloroformate in solution in 5 ml of chloroform is added dropwise and under stirring to a suspension of 1.5 g (4.90 mmol) of 1,12-bis(imidazolin-2-yl)dodecane and 1.5 ml (10.78 mmol) of triethylamine in 25 ml of chloroform cooled down by an ice bath, After which, stirring is maintained at ambient temperature overnight. The reaction mixture is then filtered and the filtrate washed successively with 120 ml of water, 120 ml of a saturated aqueous solution of sodium chloride and 2×120 ml of water. After drying over sodium sulphate, the organic phase is evaporated under reduced pressure in order to produce 2.05 g (82%) of product in the form of an oil.

NMR $^1$H (CDCl$_3$, 100 MHz), δ (ppm): 0.88 (t, 6H); 1.20 (s, 16H); 1.36-1.64 (m, 12H); 2.63 (t, 4H); 3.71 (s, 8H); 4.08 (t, 4H).

FT-IR, ν (cm$^{-1}$): 1073 and 1152 (C—O—C); 1644 (C=N); 1722 (NCO).

1,12-bis[N,N'-(isobutyloxycarbonyl)imidazolin-2-yl]dodecane: 6.4

1.35 ml (10.29 mmol) of isobutyl chloroformate in solution in 5 ml of chloroform is added dropwise and under stirring to a suspension of 1.5 g (4.90 mmol) of 1,12-bis(imidazolin-2-yl)dodecane and 1.5 ml (10.78 mmol) of triethylamine in 25 ml of chloroform cooled down by an ice bath. After which, stirring is maintained at ambient temperature overnight. The reaction mixture is then filtered and the filtrate washed successively with 120 ml of water, 120 ml of a saturated aqueous solution of sodium chloride and 2×120 ml of water. After drying over sodium sulphate, the organic phase is evaporated under reduced pressure in order to produce an oily residue. The latter, taken up in petroleum ether and left at −4° C., produces 2.26 g (91%) of product in the form of a white solid.

Melting point: <40° C.

NMR $^1$H (CDCl$_3$, 100 MHz), δ (ppm): 0.87 (d, 12H); 1.17 (s, 16H); 1.55 (m, 4H); 1.89 (quint., 2H); 2.62 (t, 4H); 3.70 (s, 8H); 3.84 (d, 4H).

FT-IR, ν (cm$^{-1}$): 1072 and 1142 (C—O—C); 1642 (C=N); 1722 (NCO).

1,12-bis[N,N'-(benzyloxycarbonyl)imidazolin-2-yl]dodecane: 6.5

0.94 ml (6.54 mmol) of benzyl chloroformate in 5 ml of chloroform is added dropwise and under stirring to a suspension of 1 g (3.27 mmol) of 1,12-bis(imidazolin-2-yl)dodecane and 0.85 ml (6.54 mmol) of triethylamine in 30 ml of chloroform cooled down by an ice bath. After which, stirring is maintained at ambient temperature overnight. The solution obtained is evaporated under reduced pressure. The precipitate isolated is subsequently extracted several times with ether. Evaporation under reduced pressure of the ether phase produces 1.02 g (54%) of product in the form of an oil crystallizing as white powder at −4° C. from ether.

Melting point: 75-76° C.

NMR $^1$H (CDCl$_3$, 100 MHz), δ (ppm): 1.23 (s, 16H); 1.60 (m, 4H); 2.68 (t, 4H); 3.77 (s, 8H); 5.16 (s, 4H); 7.35 (s, 10H).

FT-IR, ν (cm$^{-1}$): 1142 and 1299 (C—O—C); 1646 (C=N); 1714 (NCO)

MS-ES+: [M+H]$^+$: 575

1,12-bis[N,N'-(4-nitrobenzyloxycarbonyl)imidazolin-2-yl]dodecane: 6.6

1.44 g (6.70 mmol) of 4-nitrobenzyl chloroformate in solution in 10 ml of chloroform is added dropwise and under stirring to a suspension of 1 g (3.27 mmol) of 1,12-bis(imidazolin-2-yl)dodecane and 0.87 ml (6.70 mmol) of triethylamine in 20 ml of chloroform cooled down by an ice bath. After which, stirring is maintained at ambient temperature overnight. The reaction mixture is then diluted with 30 ml of chloroform then washed successively with 120 ml of water, 120 ml of a saturated aqueous solution of sodium chloride and 2×120 ml of water. After drying over sodium sulphate, the organic phase is evaporated under reduced pressure. The residue, cooled down and taken up in a minimum of chloroform, is finally crystallized at −4° C. from hexane in order to produce 2.08 g (96%) of product in the form of a white powder.

Melting point: 115-116° C.

NMR $^1$H (CDCl$_3$, 100 MHz), δ (ppm): 1.21 (s, 16H); 1.60 (m, 4H); 2.67 (t, 4H); 3.80 (s, 8H); 5.24 (s, 4H); 7.46 and 7.55 (dd, 4H); 8.17 and 8.25 (dd, 4H).

FT-IR, ν (cm$^{-1}$): 1005 and 1154 (C—O—C); 1343 and 1517 (NO$_2$); 1645 (C=N); 1724 (NCO).

MS-ES+: [M+H]$^+$: 665

1,12-bis[N,N'-(phenyloxycarbonyl)imidazolin-2-yl]dodecane: 6.7

1.26 (10.05 mmol) of phenyl chloroformate in solution in 5 ml of chloroform is added dropwise and under stirring to a suspension of 1.5 g (4.90 mmol) of 1,12-bis(imidazolin-2-yl)dodecane and 1.3 ml (10.05 mmol) of triethylamine in 25 ml of chloroform cooled down by an ice bath. After which, stirring is maintained at ambient temperature overnight. The reaction mixture is then diluted with 30 ml of chloroform, then washed successively with 120 ml of water, 120 ml of a saturated aqueous solution of sodium chloride and 2×120 ml of water. After drying over sodium sulphate, the organic phase is evaporated under reduced pressure in order to produce 2.42 g (90%) of product in the form of an oil.

NMR $^1$H (CDCl$_3$, 100 MHz), δ (ppm): 1.21 (s, 16H); 1.64 (m, 4H); 2.72 (t, 4H); 3.89 (s, 8H); 7.06-7.43 (m, 10H)

FT-IR, ν (cm$^{-1}$): 1162 and 1188 (C—O—C); 1646 (C=N); 1737 (NCO).

MS-ES+: [M+H]$^+$: 547; [M+2H]$^{2+}$/2: 274 (100%)

1,12-bis[N,N'-(4-fluorophenylyloxycarbonyl)imidazolin-2-yl]dodecane: 6.8

0.89 ml (6.70 mmol) of 4-fluorophenyl chloroformate in solution in 5 ml of chloroform is added dropwise and under stirring to a suspension of 1 g (3.27 mmol) of 1,12-bis(imidazolin-2-yl)dodecane and 0.89 ml (6.86 mmol) of triethylamine in 20 ml of chloroform cooled down by an ice bath. After which, stirring is maintained at ambient temperature overnight. The reaction mixture is then diluted with 20 ml of chloroform, then washed successively with 60 ml of water, 60 ml of a saturated aqueous solution of sodium chloride and 2×60 ml of water. After drying over sodium sulphate, the organic phase is evaporated under reduced pressure. The residue, cooled down, is finally crystallized at −4° C. from hexane in order to produce 1.70 g (85%) of product in the form of a white powder.

Melting point: 95-96° C.

NMR $^1$H (CDCl$_3$, 100 MHz), δ (ppm): 1.21 (s, 16H); 1.64 (m, 4H); 2.71 (t, 4H); 3.90 (s, 8H); 7.03 and 7.36 (d, 8H).

FT-IR, ν (cm$^1$): 1100 (C—F); 1179 (C—O—C); 1655 (C=N); 1733 (NCO).

MS–ES+: [M+H]$^+$: 583; [M+2H]$^{2+}$/2: 292 (100%)

1,12-bis[N,N'-(4-fluorophenylyloxycarbonyl)imidazolin-2-yl]dodecane dihydrochloride: 6.8, 2 HCl 1 g of 6.8 is added to 20 ml of an ethanolic solution saturated with hydrochloric acid gas. The reaction mixture stirring is then heated at 50° C. for 4 hours under vigorous. 150 ml of ether is added to the cold solution, then the mixture is left to rest in the refrigerator overnight. After decantation, the oily layer formed is taken up in 100 ml of distilled water then filtered. The filtrate is finally lyophilized in order to produce the salt in the form of a white powder.

NMR $^1$H (DMSO-d$_6$, 100 MHz), δ (ppm): 1.70 (s, 16H); 2.13 (m, 4H); 3.46 (t, 4H); 4.55 (t, 4H); 4.80 (t, 4H); 7.78 and 7.85 (d, 8H); 8.71 (s, 2H).

FT-IR, ν (cm$^{-1}$): 1692 (C=N); 1760 (NCO); 3350 (N, HCl).

1,12-bis[N,N'-(4-methoxyphenylyloxycarbonyl)imidazolin-2-yl]dodecane: 6.9

1.02 ml (6.86 mmol) of 4-methoxyphenyl chloroformate in solution in 5 ml of chloroform is added dropwise and under stirring to a suspension of 1 g (3.27 mmol) of 1,12-bis(imidazolin-2-yl)dodecane and 0.89 ml (6.86 mmol) of triethylamine in 25 ml of chloroform cooled down by an ice bath. After which, stirring is maintained at ambient temperature overnight. The isolated precipitate (triethylamine hydrochloride) is subsequently extracted several times with ether. Evaporation under reduced pressure of the ether phase produces 1.31 g (66%) of product in the form of an oil.

NMR $^1$H (CDCl$_3$, 100 MHz), δ (ppm): 1.21 (s, 16H); 1.63 (s, 4H); 2.71 (t, 4H); 3.75 (s, 8H); 3.88 (s 2H); 6.61 to 7.10 (m, 8H).

FT-IR, ν (cm$^{-1}$): 1177 and 1248 (C—O—C); 1646 (C=N); 1735 (NCO).

MS–ES+: [M+H]$^+$: 607; [M+2H]$^{2+}$/2: 304 (100%)

1,12-bis[N,N'-(4-nitrophenyloxycarbonyl)imidazolin-2-yl]dodecane: 6.10

1.38 g (6.86 mmol) of 4-nitrophenyl chloroformate in solution in 5 ml of chloroform is added dropwise and under stirring to a suspension of 1 g (3.27 mmol) of 1,12-bis(imidazolin-2-yl)dodecane and 0.89 ml (6.86 mmol) of triethylamine in 25 ml of chloroform cooled down by an ice bath. After which, stirring is maintained at ambient temperature for 5 hours. After evaporation under reduced pressure of the solution, the precipitate formed is then washed with water, then with acetone. The yellow solid obtained is subsequently crystallized by dissolving in a minimum of dichloromethane and by the slow addition of acetone. The product is isolated in the form of white crystals at 74% (1.54 g).

Melting point: 121-122° C.

NMR $^1$H (CDCl$_3$, 100 MHz), δ (ppm): 1.23 (s, 16H); 1.67 (m, 4H); 2.73 (t, 4H); 3.95 (s, 8H); 7.25 and 7.36 (dd, 4H); 8.24 and 8.32 (dd, 4H).

FT-IR, ν (cm$^{-1}$): 1185 and 1196 (C—O—C); 1349 and 1524 (NO$_2$); 1656 (C=N); 1748 (NCO).

MS–ES+: [M+H]$^+$: 637; [M+2H]$^{2+}$/2: 319 (100%)

1,12-bis[N,N'-(acetoxymethoxycarbonyl)imidazolin-2-yl]dodecane: 6.11

1 g (6.54 mmol) of acetoxymethyl chloroformate in solution in 5 ml of chloroform is added dropwise and under stirring to a suspension of 1 g (3.27 mmol) of 1,12-bis(imidazolin-2-yl)dodecane and 0.92 ml (6.54 mmol) of triethylamine in 20 ml of chloroform cooled down by an ice bath. After which, stirring is maintained at ambient temperature overnight. The reaction mixture is then washed successively with 20 ml of water, 20 ml of a 5% aqueous solution of sodium bicarbonate, then 20 ml of a saturated aqueous solution of sodium chloride. After drying over sodium sulphate, the organic phase is evaporated under reduced pressure in order to produce 2.95 g (84%) of product in the form of an oil.

NMR $^1$H (CDCl$_3$, 100 MHz), δ (ppm): 1.21 (s, 16H); 1.58 (m, 4H); 2.08 (s, 6H); 2.65 (t, 4H); 3.74 (s, 8H); 5.74 (s, 4H).

FT-IR, ν (cm$^{-1}$): 1643 (C=N); 1682 (NCO); 1736 (OCO).

MS–ES+: [M+H]$^+$: 539

1,12-bis[N,N'-((1-acetoxyethoxy)carbonyl)imidazolin-2-yl]dodecane: 6.12 a) 1,12-bis[N,N'-((1-chloroethoxy)carbonyl)imidazolin-2-yl]dodecane dihydrochloride 1.8 ml (16.75 mmol) of 1-chloroethyl chloroformate in solution in 10 ml of chloroform is added dropwise and under stirring to a suspension of 2.50 g (8.17 mmol) of 1,12-bis(imidazolin-2-yl)dodecane and 2.16 ml (16.75 mmol) of triethylamine in 40 ml of chloroform cooled down by an ice bath. After which, stirring is maintained at ambient temperature overnight. The reaction mixture is then filtered and the filtrate washed successively with 100 ml of water, 100 ml of a saturated aqueous solution of sodium chloride and 3×100 ml of water. After drying over sodium sulphate, the organic phase is evaporated under reduced pressure. The residue, cooled down, is then crystallized at −4° C. from hexane in order to produce 3.91 g (92%) of product in the form of a white powder.

NMR $^1$H (CDCl$_3$, 100 MHz), δ (ppm): 1.19 (s, 16H); 1.58 (m, 4H); 1.77 (d, 6H); 2.64 (t, 4H); 3.74 (s, 8H); 6.49 (q, 2H).

FT-IR, ν (cm$^{-1}$): 1087 (C—O—C); 1377 (CH$_3$; C—H); 1648 (C=N); 1737 (NCO).

b) 1,12-bis[N,N'-((1-acetoxyethoxy)carbonyl)imidazolin-2-yl]dodecane: 6.12

A solution of acetic acid containing 3.20 g (6.17 mmol) of 1,12-bis[N,N'-((1-chloroethoxy)carbonyl)imidazolin-2-yl]dodecane dihydrochloride and 5.9 g (18.50 mmol) of mercuric acetate is left under stirring and at ambient temperature for 72 hours. After evaporation of the solvent under reduced pressure, the reaction residue is diluted in 150 ml of chloroform, then filtered. The filtrate is then washed with 3×300 ml of a saturated aqueous solution of sodium chloride. Drying over sodium sulphate and the evaporation under reduced pressure of the organic phase produces 2.40 g (68%) of product in the form of a coloured oil.

NMR $^1$H (DMSO-$d_6$, 100 MHz), δ (ppm): 1.24 (s, 16H); 1.44 (d, 6H); 1.52 (m, 4H); 2.03 (s, 6H); 2.61 (t, 4H); 3.79 (s, 8H); 6.69 (q, 2H).

FT-IR, ν (cm$^{-1}$): 1072 and 1224 (C—O—C); 1645 (C=N); 1684 (NCO); 1733 (CO)

MS–ES+: [M+H]$^+$: 567

Diphenyl [1,12-bis(imidazolin-2-yl)dodecane]-1,12-bis-N,N'-phosphonate: 6.13

1.40 (6.70 mmol) of diphenylchlorophosphonate in solution in 5 ml of chloroform is added dropwise and under stirring to a suspension of 1 g (3.26 mmol) of 1,12-bis(imidazolin-2-yl)dodecane and 0.96 ml (6.86 mmol) of triethylamine in 25 ml of chloroform cooled down by an ice bath. After which, stirring is maintained at ambient temperature overnight. The reaction mixture is then filtered and the filtrate washed successively with 100 ml of water, 100 ml of a saturated aqueous solution of sodium chloride and 2×100 ml of water. After drying over sodium sulphate, the organic phase is evaporated under reduced pressure in order to produce 2.37 g (94%) of product in the form of an oil.

NMR $^1$H (CDCl$_3$, 100 MHz), δ (ppm): 1.20 (s, 16H); 1.62 (m, 4H); 2.58 (t, 4H); 3.79 (s, 8H); 7.17-7.34 (m, 20H).

FT-IR, ν (cm$^{-1}$): 925 (P=O); 1160 and 1184 (C—O); 1646 (C=N).

Diethyl [1,12-bis(imidazolin-2-yl)dodecane]-1,12-bis-N,N'-phosphonate: 6.14

1.49 ml (10.29 mmol) of diethylchlorophosphonate in solution in 5 ml of chloroform is added dropwise and under stirring to a suspension of 1.5 g (4.90 mmol) of 1,12-bis (imidazolin-2-yl)dodecane and 1.5 ml (10.78 mmol) of triethylamine in 25 ml of chloroform cooled down by an ice bath. After which, stirring is maintained at ambient temperature overnight. The reaction mixture is then filtered and the filtrate washed successively with 100 ml of water, 100 ml of a saturated aqueous solution of sodium chloride and 2×100 ml of water. After drying over sodium sulphate, the organic phase is evaporated under reduced pressure in order to produce 2.38 g (84%) of product in the form of an oil.

NMR $^1$H (CDCl$_3$, 100 MHz), δ (ppm): 1.15 (s, 16H); 1.23 (t, 12H); 1.54 (m, 4H); 2.37 (t, 4H); 3.60 (t, 8H); 4.00 (quintuplet, 8H).

FT-IR, ν (cm$^{-1}$): 963 (P=O); 1016 and 1268 (C—O); 1640 (C=N).

MS–ES+: [M+H]$^+$: 579; [M+H]$^{2+}$/2: 290 (100%)

1,12-bis(1-methyl imidazolin-2-yl)dodecane dihydrochloride: 7.0, 2HCl 3.9 g (10 mmol) of diethyltetradecanediimidoate dihydrochloride is refluxed with an excess of N-methyl ethylenediamine for 24 hours. After cooling the solution down, ethyl ether is added to the solution. The crystals obtained are isolated by filtration, washed in ether and dried in a desiccator, in order to produce 2.9 g (71%) of white crystals.

Melting point: 166-170° C.

NMR $^1$H (DMSO-$d_6$, 100 MHz), δ (ppm): 1.38 (m, 16H); 1.67 (m, 4H); 2.47 (t, 4H); 2.90 (s, 6H); 3.35 (s, 8H); 9.28 (m, 2H).

FT-IR, ν (cm$^{-1}$): 1600 (C=N); 3031 (C=NH, HCl); 3200 (N—H)

1,12-bis(1,4,5,6-tetrahydropyrimidin-2-yl)dodecane dihydrochloride: 8.0, 2HCl 0.51 ml (6.12 mmol) of 1,3-diaminopropane is added to a solution of 1.16 g (3 mmol) of diethyltetradecanediimidoate dihydrochloride in 15 ml of absolute ethanol. The reaction mixture is then heated under reflux for 6 hours. After the addition of 4.5 ml of water, the temperature of the reaction mixture is taken to 95° C. for 4 hours. After evaporation to dryness, the residue obtained is crystallized by the addition of ether then stirring for 48 hours. The precipitate, isolated by filtration, is then washed several times with vigorous stirring in ether and dried in a desiccator, in order to produce 0.83 g (68%) of white crystals.

Melting point: 117-119° C.

NMR $^1$H (DMSO-$d_6$, 250 MHz), δ (ppm): 1.22 (s, 16H); 1.55 (m, 4H); 1.80 (m, 4H); 2.45 (t, 4H); 3.25 (s, 8H); 9.28 (m, 2H).

1,12-bis(4-methyl imidazolin-2-yl)dodecane dihydrochloride: 9.0, 2HCl 0.44 ml (5.1 mmol) of 1,2-diaminopropane is added under stirring to a solution of 0.96 g (2.5 mmol) of diethyl tetradecanediimidoate dihydrochloride in 12 ml of anhydrous ethanol. The mixture is then heated at a temperature of 90° C. for 48 hours. After evaporation of the solvent, the residue obtained is solubilized in ethanol, then filtered. The filtrate is evaporated then ether is added and elimination under reduced pressure is carried out in order to remove the residual solvent. 0.71 g (70%) of product are then obtained in the form of a white powder.

NMR $^1$H (DMSO-$d_6$, 250 MHz), δ (ppm): 1.30 (m, 22H); 1.64 (m, 4H); 2.52 (t, 4H); 3.40 (t, 2H); 3.95 (t, 2H); 3.95 (m, 2H); 9.32 (m, 2H).

1,12-bis(4,4-dimethyl imidazolin-2-yl)dodecane dihydrochloride: 10.0, 2HCl

The reaction mixture comprising 0.96 g (2.5 mmol) of diethyl tetradecanediimidoate dihydrochloride in 12 ml of anhydrous ethanol and 0.54 ml (5.1 mmol) of 1,2-diamino-2-methylpropane is heated at 90° C. for 48 hours. The solvent is evaporated off, and the residue is solubilized in ethanol in the hot state. After cooling down to ambient temperature, the solid formed is filtered then treated with ether as compound 9.0, 2HCl in order to produce 0.76 g (70%) of product in the form of beige powder.

NMR $^1$H (DMSO-$d_6$, 250 MHz), δ (ppm): 1.24 (s, 12H); 1.32 (s, 16H); 1.62 (m, 4H); 2.50 (t, 4H); 3.54 (s, 4H); 9.30 (m, 2H).

1,12-di(3a,4.5,6.7,7a-hexahydro-1H-benzimidazo-2-yl)dodecane dihydrochloride: 11.0, 2HCl 0.96 g (2.5 mmol) of diethyltetradecanediimidoate dihydrochloride in 12 ml of anhydrous ethanol and 0.63 ml of 1,2-diaminocyclohexane are refluxed (90° C.) for 48 hours. After evaporation of the mixture, ethanol is added to the solution, filtered, and the evaporated filtrate is treated as described for compound 9.0, 2HCl. 0.82 g (67%) of crystals is obtained.

NMR $^1$H (DMSO-d$_6$, 250 MHz), δ (ppm): 1.25 (s, 16H); 1.30-1.65 (m, 16H); 1.70 (m, 4H); 2.50 (t, 4H); 3.34 (m, 2H); 4.10 (m, 2H); 9.32 (m, 2H).

1,12-bis[(1.2,4-oxadiazole)-3-yl]dodecane: 18.0

0.6 ml (4.9 mmol) of diethyltrifluoroborane is added to a suspension under stirring of 2 g (7 mmol) of bis-amidoxime 1.15 in 23.26 ml (139.86 mmol) of ethyl orthoformate. The reaction mixture is left under stirring at ambient temperature for 15 minutes then heated under reflux for 1 hour. 150 ml of ethyl acetate is added to the solution obtained, and the mixture is washed successively with water (100 ml), a saturated solution of sodium bicarbonate (100 ml) and a saturated solution of sodium chloride (100 ml). The organic phase is then dried over sodium sulphate and evaporated under reduced pressure. The residue obtained is washed with cold ether then dried in order to produce 1.50 g (70%) of product in the form of a white powder.

Melting point: 92-93° C.
NMR $^1$H (CDCl$_3$, 100 MHz), δ (ppm): 1.24 (s, 16H); 1.73 (m, 4H); 2.77 (t, 4H); 8.61 (s, 2H).
FT-IR, ν (cm$^1$): 1111 (C—O); 1558 (C=N); 3123 (=CH).

1,12-bis[(5-methyl-1,2,4-oxadiazole)-3-yl]dodecane: 18.1

A suspension under stirring of 1.5 g (4.05 mmol) of 1.22 in 30 ml of xylene, is heated at 150° C. for 2 hours. The reaction mixture is then evaporated under reduced pressure. The solid residue obtained is subsequently recrystallized from petroleum ether in order to produce, after drying in a desiccator, 1.10 g (81%) of product in the form of a white powder.

Melting point: 63-64° C.
NMR $^1$H (CDCl$_3$, 100 MHz), δ (ppm): 1.23 (s, 16H); 1.69 (m, 4H); 2.53 (s, 6H); 2.66 (t, 4H).
FT-IR, ν (cm$^{-1}$): 1581 (C—N); 1640 (C=N)

1,12-bis[(5-trifluoromethyl-1,2,4-oxadiazole)-3-yl]dodecane: 18.4

1 g (3.50 mmol) of bis-amidoxime 1.15 is added portion by portion into 20 ml (139.86 mmol) of trifluoroacetic anhydride under stirring and cooled down by an iced water bath. Stirring is maintained for 30 minutes in the cold state until 1.15 is completely dissolved. 50 ml of ether and very slowly, 100 ml of cold water (exothermal reaction) are added to the reaction mixture. The ethereal phase is then washed successively with 2×100 ml of water, 2×50 ml of a 1N soda solution and 100 ml of water. The organic phase is subsequently dried over sodium sulphate and evaporated under reduced pressure. After cooling down, the residue crystallizes in order to produce 1.39 g (90%) of product in the form of white crystals.

Melting point: <40° C.
NMR $^1$H (CDCl$_3$, 100 MHz), δ (ppm): 1.26 (s, 16H); 1.75 (m, 4H); 2.81 (t, 4H).
FT-IR, ν (cm$^{-1}$): 766 and 1150 (CF$_3$); 1519 (C—N); 1608 (C=N)

1,12-bis[(5-trichloromethyl-1,2,4-oxadiazole)-3-yl]dodecane: 18.5

A suspension under stirring of 3 g (10.49 mmol) bis-amidoxime 1.15 and 13.71 g (83.92 mmol) of trichloracetic acid in 10 ml of chloroform is heated at 85° C. until a solution is obtained. 4.70 ml (41.96 mmol) of trichloroacetyl chloride is added to the solution, three equal portions. The reaction mixture is then heated at 94° C. for 45 minutes. After cooling down, 200 ml of ethyl acetate is added, then the mixture is washed successively with a saturated solution of sodium carbonate (2×100 ml), a saturated solution of sodium chloride (2×100 ml) and 100 ml of water. The organic phase is then dried over sodium sulphate and evaporated under reduced pressure. The residue obtained is dried in order to produce 5.19 g (91%) of product in the form of a yellow powder.

Melting point: 55-56° C.
NMR $^1$H (CDCl$_3$, 100 MHz), δ (ppm): 1.26 (s, 16H); 1.76 (t, 4H); 2.78 (t, 4H).
FT-IR, ν (cm$^{-1}$): 798 and 830 (CCl$_3$); 1573 (C=N).

1,12-bis[(5-phenyl-1,2,4-oxadiazole)-3-yl]dodecane: 18.6

A suspension under stirring of 1.5 g (3.04 mmol) of 1.23 in 30 ml of xylene, is heated at 150° C. for 2 hours. The reaction solution is then decanted, then evaporated under reduced pressure. The solid residue obtained is subsequently recrystallized from petroleum ether in order to produce, after drying in a desiccator, 1.12 g (80%) of product in the form of a coloured powder Melting point: 97-98° C.
NMR $^1$H (CDCl$_3$, 100 MHz), δ (ppm): 1.25 (s, 16H); 1.78 (m, 4H); 2.77 (t, 4H); 7.48-7.54 (m, 6H); 8.06-8.14 (m, 4H).
FT-IR, ν (cm$^{-1}$): 1581 (C—N); 1640 (C=N)

1,12-bis[(5-ethyloxycarbonyl-1.2,4-oxadiazole)-3-yl]dodecane: 18.7

2.35 ml (21 mmol) of ethyl oxalyl chloride is added to a suspension under stirring of 2 g (7 mmol) of bis-amidoxime 1.15, 4 ml (49.50 mmol) of pyridine and 4 g of 4A molecular sieve in 50 ml of chloroform. The reaction mixture is then heated at 80° C. for 16 hours, then filtered and evaporated under reduced pressure. 100 ml of ethyl acetate is added to the residue, then the solution is washed successively with a saturated solution of sodium carbonate (2×50 ml), a saturated solution of sodium chloride (2×50 ml) and 50 ml of water. The organic phase is then dried over sodium sulphate and evaporated under reduced pressure. The cold residue obtained is washed with cold ethanol, then dried in order to produce 1.96 g (62%) of product in the form of a powder.

Melting point: 70-71° C.
NMR $^1$H (CDCl$_3$, 100 MHz), δ (ppm): 1.24 (s, 16H); 1.44 (t, 6H) 1.77 (m, 4H); 2.80 (t, 4H); 4.51 (quartet, 4H).
FT-IR, ν (cm$^{-1}$): 1029 and 1197 (C—O—C); 1584 (C=N); 1760 (COO)

1,12-bis[(5-carbamoyl-1.2,4-oxadiazole)-3-yl]dodecane: 18.9

2 g (4.44 mmol) of 18.7 is added to a 10% ammonium ethanol solution (90 ml). The reaction mixture, hermetically sealed, is left under stirring and at ambient temperature for 24 hours. The suspension is then filtered and washed with cold ethanol then dried. 1.58 g (91%) of product are thus isolated in the form of a yellow powder.

Melting point: 196-197° C.
NMR $^1$H (DMSO-d$_6$, 100 MHz), δ (ppm): 1.71 (s, 16H); 2.14 (m, 4H); 3.23 (t, 4H); 8.98 (s, 2H).
FT-IR, ν (cm$^{-1}$): 1573 (C—N); 1604 (C=N); 1673 (CON); 3233 and 3432 (NH$_2$)

1,12-bis[(5-cyano-1.2,4-oxadiazole)-3-yl]dodecane: 18.10

1.3 ml (9.18 mmol) of trifluoroacetic anhydride is added to a suspension cooled down to 0° C. of 1.5 g (3.83 mmol) of 18.9 and 1.55 ml (19.13 mmol) of pyridine in 60 ml of dioxane. The reaction mixture is left under stirring at ambient temperature for 16 hours. The solution obtained is then diluted with 150 ml of ethyl acetate, then washed successively with water (100 ml) and with a saturated sodium chloride solution (2×100 ml). The organic phase, dried over sodium sulphate and evaporated under reduced pressure, produces 0.83 g (61%) of product in the form of a coloured oil.

NMR $^1$H (CDCl$_3$, 100 MHz), δ (ppm): 1.24 (s, 16H); 1.73 (m, 4H); 2.81 (t, 4H).

FT-IR, ν (cm$^{-1}$): 1561 (C=N); 2260 (CN)

1,12-bis(N,N'-dibenzyloxycarbonylguanidino)dodecane: 12.1

A solution of 1 g (5 mmol) of 1,12-diaminododecane and 3.76 g (10.5 mmol) of N,N'-di-benzyloxycarbonyl-S-methylisothiourea in 70 ml of tetrahydrofuran is heated between 60 and 70° C. for 24 hours. After which, the solvent is evaporated under reduced pressure. The residue obtained is then taken up in dichloromethane and washed successively with an 5% aqueous solution of sodium bicarbonate, a saturated aqueous solution of sodium chloride and water. The organic phase is subsequently dried over sodium sulphate, evaporated under reduced pressure, and purified by chromatography on a silica column (DCM). The different fractions, combined and evaporated under reduced pressure, produce a yellow oil which crystallizes from the ether in order to produce 2.4 g (58%) of product in the form of a white powder.

Melting point: 97-98° C.

NMR $^1$H (CDCl$_3$, 100 MHz), δ (ppm): 1.24 (s, 16H); 1.54 (s, 4H); 3.40 (q, 4H); 5.11 (s, 4H); 5.16 (s, 4H); 7.15-7.54 (m, 20H); 8.28 (t, 2H); 11.73 (s, 2H)

FT-IR, ν (cm$^{-1}$): 1054 and 1130 (C—O); 1651 (C=N); 1736 (NCO); 3130 (NHCO); 3333 (NH)

MS–FAB$^+$: [M+H]$^+$: 821; [M+2H]$^{++}$/2: 412

1,12-bis(N,N'-di-tert-butyloxycarbonylguanidino)dodecane: 12.2

A mixture of 1 g (5 mmol) of 1,12-diaminododecane and 3.19 g (11 mmol) of N,N'-di-tert-butyloxycarbonyl-S-methylisothiourea in 100 ml of methanol, is heated between 50 and 60° C. for 48 hours. After evaporation under reduced pressure of the solution, the residue obtained is taken up in 100 ml of DCM and washed successively with a 5% aqueous solution of NaHCO$_3$ (2×100 ml), water (2×100 ml) and 100 ml of a saturated solution of NaCl. The organic phase is then dried over sodium sulphate, evaporated under reduced pressure and purified on silica (DCM/MeOH 98%) in order to produce 2.50 g (73%) of product crystallizing from petroleum ether in the cold state in the form of a powder.

Melting point: 114-116° C.

NMR $^1$H (CDCl$_3$, 100 MHz), δ (ppm): 1.24 (s, 16H); 1.47 (s, 36H); 1.61 (m, 4H) 3.35 (q, 4H); 8.27 (t, 2H); 11.48 (s, 2H)

FT-IR, ν (cm$^{-1}$): 1028 and 1138 (C—O); 1670 (C=N); 1740 (NCO); 3132 (NHCO); 3314 (NH)

MS–ES+: [M+H]$^+$: 685

1,12-bis[N,N'-(2-amino-3,4,5,6-tetrahydropyrimidyl)]dodecane dihydroiodide: 16.0, 2HI The reaction mixture, comprising 0.72 g (3.6 mmol) of 1,12-dodecanediamine, 1.86 g (7.2 mmol) of 2-methylsulphanyl-3,4,5,6-tetrahydropyrimidinium iodide and 0.5 ml (3.6 mmol) of triethylamine in 20 ml of acetonitrile is heated under reflux for 22 hours. After cooling down to ambient temperature, the reaction solvent is evaporated off and the residue is chromatographed on a silica column (CH$_2$Cl$_2$/CH$_3$OH/NH$_4$OH 89:10:1). 0.91 g of guanidinium salt is obtained, i.e. a yield of 41%.

NMR $^1$H (CD$_3$OD, 100 MHz), δ (ppm): 1.49 (m, 20H); 2.13 (m, 4H); 3.33 (m, 4H); 3.56 (m, 8H).

MS–FAB+: [M+H]$^+$: 365; [M+H+HI]$^+$:493

1,12-bis[N,N'-(5,5-dimethyl-3,4,5,6-tetrahydropyrimidin-2-yl)amino]dodecane dihydroiodide: 17.0, 2HI The reaction mixture, comprising 0.72 g (3.6 mmol) of 1,12-dodecanediamine, of 2.06 g (7.2 mmol) of 5,5-dimethyl-2-methylsulphanyl-3,4,5,6-tetrahydropyrimidinium hydroiodide and 0.5 ml (3.6 mmol) of triethylamine in 20 ml of acetonitrile is heated under reflux for 22 hours. After cooling down to ambient temperature, the reaction solvent is evaporated off and the residue is chromatographed on a silica column (CH$_2$Cl$_2$/CH$_3$O/NH$_4$OH 89:10:1). 0.91 g of salt are obtained, i.e. a yield of 36%.

NMR $^1$H (CD$_3$OD, 100 MHz), δ (ppm): 1.17 (s, 12H); 1.49 (m, 20H); 3.07 (s, 8H); 3.23 (m, 4H).

[1-[N-(5,5-dimethyl-3,4,5,6-tetrahydropyrimidin-2-yl)amino]-12-[N'-(3,4-dihydro-2H-pyrrol-5-yl)amino]]dodecane ditrifluoroacetate: 25.0, 2TFA The reaction mixture comprising 1 mmol of 1-[N-(5,5-dimethyl-3,4,5,6-tetrahydropyrimidinium-2-yl)amino]dodecane-12-ammonium ditrifluoroacetate, 1 mmol (1 eq.) of 3,4-dihydro-5-methoxy-2H-pyrrole and 0.5 ml of triethylamine in 10 ml of absolute ethanol is heated under reflux for 20 hours. After cooling down to ambient temperature, the reaction mixture is evaporated to dryness and chromatographed on a silica column (CH$_2$Cl$_2$/CH$_3$OH/NH$_4$OH 85:13:2) in order to produce the product, in the form of an oil, with a yield of 65%.

NMR $^1$H (CD$_3$OD, 360 MHz), δ (ppm): 1.12 (s, 6H); 1.36 (m, 16H); 1.60 (n, 2H); 1.69 (m, 2H); 2.28 (m, 2H); 2.93 (m, 2H); 3.09 (s, 4H); 3.22 (m, 2H); 3.31 (m, 2H); 3.75 (m, 2H).

MS–ES$^+$: [M+H]$^+$: 378; [M+H+TFA]$^+$: 492; [M+2H]$^{++}$/2: 189.5

1,12-bis[N,N'-(3,4-dihydro-2H-pyrrol-5-yl)amino]dodecane: 21.0

2.5 g (25.25 mmol) of 2-methoxypyrroline is added to a solution of 2.76 g (10.1 mmol) of 1,12-diaminododecane hydrochloride in 70 ml of absolute ethanol. The reaction mixture is left under stirring and at ambient temperature for 24 hours. The solution is subsequently evaporated under reduced pressure and the residue after cooling down, is taken up in 100 ml of water, then alkalinized with a 0.1 N soda solution. After which, the precipitate formed is separated, washed in water, then ether and dried in a desiccator. 3.27 g (97%) of the expected product is obtained in the form of a white powder.

Melting point: 155-156° C.

NMR $^1$H (CDCl$_3$, 100 MHz), δ (ppm): 1.23 (s, 16H); 1.49 (m, 4H); 1.89 (quint., 4H); 2.38 (t, 4H); 3.21 (t, 4H); 3.43 (s, 2H); 3.62 (t, 4H)

FT-IR, ν (cm$^{-1}$): 1630 (C=N); 3049 and 3221 (NH)

1,12-bis(N,N'-acetamidinyl)dodecane: 20.0

A mixture of 2 g (10 mmol) of 1,12-diaminododecane and 2.47 g (20 mmol) of ethylacetimidate hydrochloride in 25 ml of anhydrous dioxane is heated under reflux for 24 hours. After cooling down to ambient temperature, an 1N aqueous KOH solution is added which leads to the formation of a precipitate. This precipitate is washed with methanol in the hot state, then filtered. After several hours in a desiccator, 2.06 g (7.3 mmol) of product are obtained, i.e. a yield of 73%.

Melting point: 92-97° C.
NMR$^1$H (DMSOd$_6$, 250 MHz), δ (ppm): 1.3 (m, 16H); 1.5 (m, 4H); 1.8 (s, 6H); 2.9 (t, 4H); 5.5 (m, 2H)

1,12-bis(N,N'-hydroxyacetamidinyl)dodecane, 20.1 and its dichlorohydrate, 20.1, 2HCl.

10 g (50 mmol) of 1,12-diaminododecane are added to a solution of 12.9 g (125 mmol) of ethyl N-hydroxyacetimidate in 125 ml of ethanol. The reaction mixture is heated to 80° C. for four days. After cooling, the resulting precipitate is separated, washed several times with ethanol and then with ether, dried in a desiccators and re-crystallised in ethanol to give 7.26 g (46%) of hydroxyacetamidinyl 20.1 in the form of a white powder (melting point 150-151° C.)

1 g of hydroxyacetamidinyl 20.1 is dissolved in 20 ml of anhydrous ethanol saturated with hydrochloric acid gas. The mixture is vigorously stirred and heated to 50° C. for two hours. To the cold solution is added 100 ml of anhydrous ether and the mixture is left to settle. The resulting solid is separated, dried, dissolved in 100 ml of distilled water and then filtered. The aqueous filtrate is freeze-dried to give the product in the form of a white powder.

$^1$H NMR (DMSO-d$_6$, 100 MHz): 1.72 (s. 16H, H$_3$-H$_{10}$); 1.96 (s, 4H, H$_2$ and H$_{11}$); 2.62 (s, 6H, 2H$_2$: 3.86 (q, 4H, H$_1$ and H$_{12}$); 9.30 (t. 2H. 2NH); 11.40 (s, 2H, 2NOH); 12.92 (s, 2H, 2C=NOH, HCl).
FT-IR: 1683 (C=N); 3002; 3142 and 3202 (NH; C=NOH, HCl and NOH

1,12-bis(N,N'-methoxyacetamidinyl)dodecane, 20.2

To a hydroxyl-alcoholic soda solution [prepared from 0.45 g (11.15 mmol) of soda and 25 mL ethanol/water (4:1)} is added 1 g (3.18 mmol) hydroxyacetamidinyl 20.1. After 30 minutes of stirring, 0.42 mL (6.68 mmol) methyl iodide is added dropwise to the reaction suspension. The mixture is stirred at room temperature for 24 hours. The cloudy solution is then filtered and the filtrate is evaporated under reduced pressure. The residue obtained is redissolved in 50 mL chloroform and washed with a saturated aqueous solution of NaCl (2×100 mL). The organic phase is dried over sodium sulphate and evaporated under reduced pressure to give 1.05 g (96%) of methoxyacetamidinyl in the form of a coloured oil.

$^1$H NMR (CDCl$_3$, 100 MHz): 1.24 (s, 16H, H$_3$-H$_{10}$); 1.45 9m, 4H, H$_2$ and H$_{11}$; 1.83 (s, 6H, 2H$_{2'}$); 3.05 (q, 4H, H$_1$ and H$_{12}$); 3.70 (s, 6H, 2H$_3$.): 5.03 (t, 2H, 2NH).
ES$^+$SM: 343 [M+H$^+$]; 172 (100%) [M+2H$^+$)/2].
FT-IR: 1637 (C=N); 3264 (NH).

1-12-bis(N,N'-acetoxyacetamidinyl)dodecane: 20.8

1 g (3.18 mmol) of hydroxacetamidinyl 20.1 is added in small portions to a stirred solution of 12 ml (127.4 mmol) acetic anhydride cooled at 0°. The mixture is stirred for 2 hours at room temperature. A 100 ml of chloroform are added to the reaction mixture. The solution is washed successively with 2×100 ml of a solution of aqueous saturated sodium chloride, 3×100 ml of soda solution 2N and 2×100 ml of water. The organic phase is then dried over sodium sulphate and evaporated and evaporated under reduced pressure. 30 ml of ether are added to the oily cold residue and the solution is left in the refrigerator for 16 hours. The resulting solid is then triturated in ether and separated. The powder obtained is finally washed with ether and dried to give 1.12 g (89%) of actoxyacetamidinyl in the form of a white powder.

Melting point 68-69° C.
$^1$NMR (CDCl$_3$, 100 NHz): 1.24 (s, 16H, H$_3$-H$_{10}$); 1.44 (m, 4H, H$_2$ and H$_{11}$); 1.92 (s, 6H, 2H$_{2'}$); 2.11 (s, 6H, 2H$_{4'}$); 3.10 9q. 4H, H$_1$ and H$_{12}$); 5.04 9t, 2H, 2NH).
ES$^+$SM: 399 (100%) [M+H$^+$}; 200 [(M+2H$^+$)/2
FT-IR: 1623 (C=N); 1742 (OCO): 3333 (NH)

1,12-bis(N,N'-benzoyloxyacetamidinyl)dodecane, 20.9

To a stirred suspension of 1 g (3.18 mmol) of hydroxyacetamidinyl 20.1 and 0.94 ml (6.68 mmol) of triethylamine in 30 ml of chloroform, cooled at 0° C., are added dropwise 0.78 ml (6.68 mmol) of benzoyl chloride in 5 ml of chloroform. The mixture is stirred for 3 hours at room temperature. The reaction mixture is then washed with 2×100 ml of water and then with 100 ml of a saturated solution of sodium chloride. The organic phase is then dried over sodium sulphate and evaporated under reduced pressure. The oily residue is left over night in a refrigerator. The resulting solid is triturated with cold ether, washed with ether and then separated and dried to give 1.27 g (77%) of benzoyloxyacetamidinyl in the form of white powder.

Melting Point 95-96° C.
$^1$H NHR (CDCl$_3$, 200 MHz): 1.23 (s, 16H, H$_3$-H$_{10}$); 1.51 (m, 4H, H$_2$ and H$_{11}$); 2.02 (sm 6H, 2H$_{2'}$); 3.15 (q, 4H, H$_1$ and H$_{12}$); 5.19 (t, 2H, 2NH); 7.34-7.54 [m, 6H, 2(6H, 2(H$_6$-H$_8$)]; 7.93-8.03 [dd, 4H, 2(H$_5$ and H$_9$)]
FT-IR: 1279 (C—O—C); 1622 (C=N); 1714 (OCO); 3385 (NH).
ES$^+$SM: 523 (100%) [M+H$^+$]; 262 [M+2H$^+$)/2.

1,12-bis(N,N'-ethylcarbamoyloxyacetamidinyl)dodecane: 20.10

To a stirred suspension of 1 g (3.18 mmol) hydroxyacetamidinyl 20.1 and 0.45 g (30.18 mmol) of potassium carbonate in 40 ml of chloroform is added dropwise 0.53 ml (6.69 mmol) ethylisocyanate. The mixture is stirred overnight at room temperature. The reaction mixture is filtered and the filtrate is washed with 3×100 ml of water. The organic phase is then dried over sodium sulphate and evaporated under reduced pressure to give 1.32 g (91%) of ethyl carbamoyloxyacetamidinyl in the form of a coloured oil.

1H NMR (CDCl$_3$, 100 MHz): 1.14 (t, 6H, 2H$_{5'}$); 1.22 (s. 16H, H$_3$-H$_{10}$); 1.44 (m 4H, H$_2$ and H$_{11}$); 1.84 (s, 6H, 2H$_{2'}$); 3.07 (q, 4H, H$_1$ and H$_{12}$); 3.26 (quintuplet, 4H, 2H$_4$); 5.33 (t, 2H, 2NH); 6.49 (t, 2H, 2NHCO).
FT-IR: 1215 (C—O); 1641 (C=N); 1705 (OCON); 3345 (NHCO); 3398 (NH).

1,12bis-(N,N'-phenylcarbamoyloxyacetamidinyl)dodecane: 20.11

To a stirred solution of 1 g (3.18 mmol) of hyroxyacetamidinyl 20.1 and 0.45 g (3.18 mmol) of potassium carbonate in 40 ml of chloroform is added dropwise 0.73 ml (6.69 mmol) of phenylisoyanate. The mixture is stirred overnight at room temperature. The reaction mixture is then filtered and the filtrate is washed with 3×100 ml of water. The organic phase is then dried over sodium sulphate and evaporated under reduced pressure. The solid residue obtained is washed several times with ether and then dried in a desiccators to give 1.53 g (87%) of phenylcarbomoyloxyacetamidinyl in the form of a white powder.

Melting point: 103-104° C.

$^1$H NMR (CDCl$_3$, 100 MHz): 1.26 (s, 16H, H$_3$-H$_{10}$); 1.51 (m, 4H, H$_2$ and H$_{11}$); 1.94 (s, 6H, 2H$_{2'}$); 3.13 (q, 4H, H$_1$ and H$_{12}$); 5.46 (t, 2H, 2NH); 7.0-7.52 (m, 10H, H aromatique); 8.61 (s, 2H, 2NHCO).

FT-IR: 1663 (C=N); 1717 (OCON); 3291 (NHCO); 3443 (NH).

ES$^+$SM: 457 (100%) [M+H$^+$]; 299 [(M+2H$^+$)/2.

1,12-bis(N,N'-methylsulfonyloxyacetamidinyl)dodecane: 20.12

To a stirred suspension of 1 g (3.18 mmol) of hydroxyacetamidinyl 20.1 and 0.55 ml (6.68 mmol) of pyridine in 30 ml of chloroform cooled to between 0° C. and 5° C. in an ice bath is added dropwise 0.52 ml (6.68 mmol) of methysulfonyl chloride in 5 ml of chloroform. The mixture is stirred for four hours between 10 and 15° C. The reaction mixture is then washed with 3×100 ml of water. The organic phase is dried over sodium sulphate and evaporated under reduced pressure. The oily residue is left over night in the refrigerator. The resulting solid is triturated with cold ether, washed with ether and then separated and dried to give 1.33 g (89%) of methylsulfonyloxyacetamidinyl in the form of a white powder.

Melting point 67-68° C.

$^1$H NMR (CDCl$_3$, 100 MHz): 1.25 (s, 16H, H$_3$-H$_{10}$); 1.51 (m, 4H, H$_2$ and H$_{11}$); 1.91 (s, 6H, 2H$_{2'}$); 3.11 (q, 6H, 2H$_{3'}$); 3.15 (q, 4H, H$_1$ and H$_{12}$); 5.23 (t, 2H, 2NH)

FT-IR: 1637 (C=N); 3302 (NH).

ES$^+$SM: 471 (100%) [M+H$^+$]

[1,12-bis(acetamidinyl)dodecane]-1,12-bis-N,N'-diethyl phosphate, 20.13

To a stirred suspension of 1 g (3.18 mmol) hyroxyacetamidinyl 20.1 and 0.94 ml (6.68 mmol) of triethylamine in 30 ml of DMF, cooled to between 0 and 5° C., is added dropwise 0.97 ml (6.68 mmol) of diethychlorophonate in 5 ml of chloroform. The mixture is stirred over night. The reaction mixture is filtered and the filtrate is re-dissolved in 100 mL ethyl acetate. The organic phase is washed with 3×100 ml of water and then dried over sodium sulphate and evaporated under reduced pressure. The residue is redissolved in 100 ml of chloroform and washed again with 3×100 ml of water, dried over sodium sulphate and evaporated under reduced pressure. The residue is redissolved in 100 mL chloroform, washed again with 3×100 mL water, dried over sodium sulphate and evaporated under reduced pressure to give 1.13 g (61%) of 20.13 in the form of a coloured oil.

$^1$H NMR (CDCl$_3$, 100 MHz): 1.25 (s, 16H, H$_3$-H$_{10}$); 1.33 (t, 12H, 4H$_4$); 1.43 (m, 4H, H$_2$ and H$_{11}$); 1.87 (s, 6H, 2H$_{2'}$); 3.08 (q, 4H, H$_1$ and H$_{12}$); 4.18 (quint, 8H, 4H$_{3'}$) 5.28 (t, 2H, 2NH).

FT-IR: 1634 (C=N); 3316 (NH).

1,12-bis[N,N'(3-methyl-1,2,4-oxadiazol-5(4H)-one)-3-yl]dodecane: 20.14

To a stirred suspension of 1 g (3.18 mmol) of hydroxyacetamidinyl 20.1 and 0.45 g (3.18 mmol) of potassium carbonate in 30 ml of chloroform is added dropwise 0.50 ml (6.68 mmol) of methchloroformiate in 5 ml of chloroform. The reaction is stirred for 1 hour at room temperature and then the suspension is heated to about 50° C. for 45 minutes. The reaction mixture is cooled and then filtered, washed with 3×100 ml of water. The organic phase is then dried over a sodium sulphate and evaporated under reduced pressure. The residue is left overnight in the refrigerator. The resulting solid is finally triturated in cold ether, washed with ether and then separated and dried to give 0.92 g (79%) of oxadiazolone in the form of a white powder.

Melting point: 53-54° C.

$^1$H NMR (CDCl$_3$, 00 MHz): 1.24 (s, 16H, H$_3$-H$_{10}$); 1.64 (s, 4H, H$_2$ and H$_{11}$); 2.24 (s, 6H, 2H$_{2'}$); 3.52 (t, 4H, H$_1$ and H$_{12}$).

FT-IR: 1559 (C=N); 1754 (OCO)

1,12-bis[N,N'-2-hydroxyacetamidinyl]dodecane 26.0 a) Hydroxyacetonitrile or Glycolonitrile

To an aqueous solution (60 ml) of 15 g (306 mmol) of sodium cyanide, cooled to 0° C., is added dropwise, 22.73 g (303 mmol) of a sodium of formaldehyde (40% in water). The reaction is stirred for 30 minutes at this temperature.

The pH of the solution is successively adjusted to 2 with H$_2$SO$_4$ 7.5N (45 ml) and to 5 with Na$_2$CO$_3$. The sodium sulphate, which is eventually formed, is dissolved by adding water and the solution is then extracted with ether (4×200 ml). The organic phase is dried over anhydrous sodium sulphate and evaporated under reduced pressure to give 13.13 g (76%) of hydroxyacetonitrile in the form of the coloured oil. This oil, unpurified, is used directly. The oil decomposes at room temperature after 24 hours.

1H NMR (CDCl$_3$ 100 MHz): 2.30 (s, 1H, OH); 4.34 (s, 2H, CH$_2$).

FT-IR: 2259 (C=N); 3425 (OH).

b) Ethylhyroxyacetimidate Chlorohydrate

HCL gas is bubbled through a solution of 20 ml of anhydrous ethanol, 40 ml of anhydrous ether and 9 g (158 mmol) of hydroxyacetonitrile cooled to 0° C., for 1 hour and 30 minutes. The reaction precipitate is separated and washed several times with ether and then dried in the dessicator to give 19.52 g (89%) of ethyl hydroxyacetimidate chlorohydrate in the form of a white powder.

$^1$H NMR (DMSO-d$_6$, 100 MHz): 1.80 (t, 3H, CH$_3$); 4.80 (s, 2H, CH$_2$); 4.85 (q, 2H, CH$_2$); 11.73 (s1, 2H, NH, HCl).

FT-IR: 1645 (C=N); 3119 (OH); 3229 (NH, HCl)

1,12-bis(N,N' 2-hydroxyacetamidinyl)dodecane: 26.0

To a solution of 3.07 g (22 mmol) of ethylhydroxyacetimidate chlorohydrate in methanol (50 mL) is added 2 g (10 mmol of 1,12-diaminododecane. The reaction mixture is stirred at room temperature for 24 hours. The solution is then evaporated under reduced pressure. The cold residue is then re-dissolved in 100 ml of water and then basified cold with NaOH 0.5N. The resulting precipitate is separated and washed with water, with acetone several time, then with ether, and separated, to give after drying, 2.55 g (81%) of 2-hydroxyacetamidinyl 26,0 in the form of a white powder.

Melting point: 99-100° C.

$^1$H NMR (CD$_3$OD, 250 MHz): 1.00 (s, 16H, H$_3$-H$_{10}$); 1.27 (m, 4H, H2 and H11): 2.84 (t, 4H, H$_1$ and H$_{12}$): 2.98 (s, 2H, 2 OH); 3.70 (s, 4H, 2H$_{2'}$)

FT-IR: 1605 (C=N); 3072 (OH); 3290 and 3388 (2NH)

ES$^+$SM: 315 [M+H$^+$]

1,12-bis[N,N'-(2-iminopyrrolidinyl)]dodecane: 24.0

1.64 g (5 mmol) of 1,12-dibromododecane is added by small fractions to a mixture of 2.21 g (26 mmol) of pyrrolidin-2-one and 0.23 g (10 mmol) of sodium heated at 90° C. under nitrogen. This reaction mixture is then heated under stirring at 120° C. for 4 hours. After cooling down to ambient temperature, 40 ml of water are added and the solution is extracted with 40 ml of DCM. The organic phase is then washed with a saturated aqueous solution of NaCl, dried over $MgSO_4$ then evaporated under reduced pressure. Purification on a silica column (eluent DCM-methanol, [18-1]) followed by co-evaporation at ambient temperature with an ether-hexane mixture produces 0.655 g of 1,12-bis[N,N'-(pyrrolidin-2-one-1-yl)]dodecane, with a yield of 39%. 0.18 ml (2 mmol) of sulphonyl chloride isocyanate in 3 ml of chloroform is added dropwise to a mixture of 0.336 g (1 mmol) of this product in 3 ml of chloroform under nitrogen. The reaction mixture is heated at 77° C. for 6 hours. After the addition of 4.5 ml of water, the temperature of the reaction mixture is then taken to 95° C. for 4 hours. After which, 5 ml of water is added and the solution is washed with 2×5 ml of DCM. The aqueous phase is then neutralized by an 1N aqueous solution of KOH and the solid is filtered, washed in ether then dried for 1 hours 30 minutes in a desciccator in order to produce 0.135 g (40%) of product.

Melting Point: 53-55° C.

NMR $^1$H (DMSOd$_6$, 250 MHz) δ (ppm): 1.3 (m, 16H); 1.5 (m, 4H); 1.8 (q, 4H); 2.3 (t, 4H); 3.2 (t, 4H) 3.3 (t, 4H); 8.0 (s, 2H)

Study of the Pharmacological Activities of the Compounds According to the Invention.

A. Antimalarial Activity In Vitro Against *P. Falciparum* and In Vivo in Mice Infected with *P. Vinckei*

Tables 4 and 5 hereafter show the results of the $IC_{50}$ values in μM and of $ED_{50}$ (mg/kg) obtained with compounds of the invention.

TABLE 4

Series A

| Compound | $IC_{50}$ (μM) | $ED_{50}$ (mg/Kg) P. vinckei |
|---|---|---|
| 1.0, 2 HCl | 0.3 10$^{-3}$ | nd |
| 1.1 | nd | nd |
| 1.2 | 0.3 | ip 33 |
| 1.4 | 0.5 | nd |
| 1.5 | 0.4 | nd |
| 1.13 | 11 | ip < 20* |
| 1.15 | 3.5 | po = 120 |
| 1.16 | 6.8 | nd |
| 1.17 | 1.2 | nd |
| 1.18 | 1.1 | nd |
| 1.19 | 3.6 | nd |
| 1.22 | 1.4 | nd |
| 1.23 | 1.1 | nd |
| 1.24 | 0.2 | po = 90 |
| 1.27 | 9.2 | nd |
| 1.28 | 0.2 | nd |
| 1.30 | 20 10$^{-3}$ | ip = 20 |
| 2.0, 2 HCl | 0.7 10$^{-3}$ | ip = 1.1* po = 40* |
| 3.0 | 4.9 10$^{-3}$ | nd |
| 4.0, 2 HCl | 6.3 10$^{-3}$ | nd |
| 5.0 | 0.1 | nd |
| 6.0 | 2 10$^{-3}$ | ip = 34* po = 62* |
| 6.1 | nd | nd |
| 6.5 | 12.0 | ip < 20* po ≈ 100* |
| 6.8 | 69.5 | nd |
| 7.0, 2 HCl | 43 10$^{-3}$ | nd |
| 8.0, 2 HCl | 2.3 10$^{-3}$ | ip = 1.7* |
| 9.0, 2 HCl | 1 10$^{-3}$ | ip = 7* po = 60* |
| 10.0, 2 HCl | 1 10$^{-3}$ | ip = 6* po = 95* |
| 11.0, 2 HCl | 3 10$^{-3}$ | ip = 8* po = 105* |
| 12.0, 2 HBr | 0.3 10$^{-3}$ | nd |

TABLE 4-continued

Series A

| Compound | $IC_{50}$ (μM) | $ED_{50}$ (mg/Kg) P. vinckei |
|---|---|---|
| 12.2 | 1.9 | nd |
| 13.0, 2 HI | 1.6 10$^{-3}$ | nd |
| 14.0, 2 HCl | 21 10$^{-3}$ | nd |
| 15.0, 2 HBr | 1.7 10$^{-3}$ | ip = 0.35* po = 45* |
| 16.0, 2 HI | 0.1 10$^{-3}$ | nd |
| 17.0, 2 HI | 0.6 10$^{-3}$ | nd |

*tested after 2 administrations of the compound per day for 4 days

TABLE 5

Series B

| Compound | $IC_{50}$ (μM) | $ED_{50}$ (mg/Kg) P. vinckei |
|---|---|---|
| 20.0 | 2 10$^{-3}$ | ip = 2.3* po nd |
| 20.1 2 HCl | 0.31 | ip = 9.2 po = 90 |
| 20.2 | 4.35 | ip = 10 po = 110 |
| 20.12 | 12.10$^3$ | ip = 4.7 po = 42 |
| 20.14 | 7.1 | ip = 9 po = 62 |
| 21.0 | 3.8 10$^{-3}$ | ip = 2.8* po = 85* |
| 22.0, 2 HCl | 3 10$^{-3}$ | nd |
| 23.0 | 2.2 10$^{-3}$ | nd |
| 24.0 | 4 10$^{-3}$ | nd |
| 25.0, 2 TFA | 1.9 10$^{-3}$ | nd |
| 26.0 | 9.15 10$^3$ | nd |

*tested after 2 administrations of the compound per day for 4 days

The $IC_{50}$ is the concentration which inhibits 50% of the growth in vitro of *P. falciparum* (the $IC_{50}$ measurements were determined according to the method of Desjardins in which the incorporation of [$^3$H] hypoxanthine in the nucleic acids serves as a cell viability index) (FIG. 1), the $ED_{50}$ is the effective dose for inhibiting 50% of the growth in vivo of *P. vinckei* according to a 4-day suppression test.

TI corresponds to the therapeutic index, TI=$LD_{50}$ (semi chronic)/$ED_{50}$; ip: intraperitoneal administration; po: per os.

These results show that the compounds of the invention have strong antimalarial and antibabesia activities in vitro and in vivo as well as a good tolerance and good absorption.

B. Pharmacokinetic Parameters in Mice

The results are given hereafter of the pharmacokinetic parameters after administration by intra-peritoneal or oral route in mice for compound 6.0.

For determination of the serum level, bio-tests were used ex vivo: briefly, the medicament is administered to the animal, then blood samples are repeatedly taken. The sera are decomplemented for 30 minutes at 56° C. The active metabolite content is then determined by incubation of different concentrations (dichotomous dilution) of each serum, in the presence of suspensions of erythrocytes infected with *P. falciparum*, according to the method of DESJARDINS with [$^3$H] hypoxanthine.

The results are expressed in $IS_{50}$, which corresponds to the percentage of serum (containing an active metabolite) capable of inhibiting 50% of the growth of *P. falciparum*.

This value is then converted into serum concentration (usually expressed in ng/ml), by testing the active compound directly (without passing via the animal), on the same suspension infected with P. falciparum and by determining its IC$_{50}$ value (in ng/ml) [serum count =IC$_{50}$] (in ng/ml)×100/ SI$_{50}$ (in %)].

The results are expressed in log (serum count of medicaments), as a function of time, which allows the evaluation of the half-time for the distribution to the serum compartment t$_{1/2(d)}$; the half-time for the elimination of the serum compartment (t$_{1/2(e)}$); of C$_0$, corresponding to the serum count extrapolated to the origin in the elimination phase; of AUC (which indicates the quantity of drug circulating in the bloodstream); and the relative bio-availability in the administration method by oral route, versus the method by intraperitoneal route [AUC (po)/AUC (ip)] which signifies the degree of absorption by oral route.

Pharmacokinetics of 6.0

Doses of 17 and 300 mg per kg of 6.0 were administered to mice, by intraperitoneal route and by oral route, which corresponds to LD$_{50}$/3.

The compound is solubilized in 10% DMSO. The results are given in Table 4.

The semi-logarithmic representation makes it possible to determine the main pharmacokinetic parameters of the active metabolite for the two administration routes. The pharmacokinetic parameters are C$_0$=50 ng/ml, t$_{1/2}$=16 hours, AUC=310 ng.h/ml after ip administration of 17 mg/kg, and C$_O$=80 ng/ml, t$_{1/2}$=17 hours, AUC=170 ng.h/ml after oral administration of 300 mg/kg.

Pharmacokinetics of 21.0

Compound 21.0 was administered to mice in doses of 15 and 100 mg/kg, by intraperitoneal route and by oral route respectively, LD$_{50}$/3 ip and LD$_{50}$/4 po.

After intraperitoneal administration of 15 mg/kg, C$_0$ of 24 ng/ml is obtained with t$_{1/2}$ of approximately 35 hours.

By oral route at 100 mg/kg, C$_0$ is 16 ng/ml. The apparent t$_{1/2}$ is 36 hours.

C. Antibabesia Activities of the Compounds

The products 6.0, 22.0, and 2.0 were also evaluated in vitro for their activities against Babesia divergens and B. canis. In both cases, the compounds 6.0, 22.0, and 2.0 proved to be particularly active (IC$_{50}$<50 nM). These results indicate an powerful antibabesia activity for this type of compounds.

The invention claimed is:

1. A pharmaceutical composition comprising a pharmaceutically effective amount of at least one compound of the formula (I)

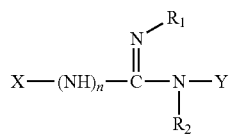

(I)

in which
X represents a group of formula (II)

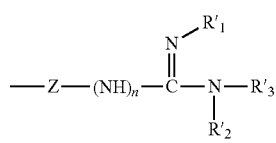

(II)

where Z is a —(CH$_2$)$_m$ group, with m=8 to 21, n=0 or 1 and Y=R$_3$,

R$_1$ and R'$_1$, identical to or different from one another, being chosen from H, alkyl, OH, O-alkyl, O-aryl, O—CO-alkyl, O—CO-aryl, OSO$_2$-alkyl, OSO$_2$-aryl, OSO$_2$-heterocycle, O—CO—S-alkyl, O—CO—NH-alkyl, O—CO—O-alkyl, O—CO—O-aryl, O—CO—S-aryl, O—CO—NH-aryl, PO(O-alkyl)$_2$, PO(O-aryl)$_2$, CO—O—CH$_2$-aryl, or cycloalkyl, R$_2$ and R'$_2$, identical to or different from one another, being chosen from H, alkyl, CO—O—CH$_2$-aryl, CO—O-alkyl, or cycloalkyl, R$_3$ and R'$_3$, identical to or different from one another, representing H, alkyl, CO—O-aryl, COO—CH(R)—O—CO-alkyl, PO(O-alkyl)$_2$, PO(O-aryl)$_2$, PO(ONa)$_2$, or CO—O—CH(R)-aryl, R being H or alkyl, or R$_1$ and R$_2$, and/or R'$_1$ and R'$_2$, or R$_2$ and R$_3$ and/or R'$_2$ and R'$_3$, or R$_1$, R$_2$ and R$_3$ and/or R'$_1$, R'$_2$ and R'$_3$, together form a nitrogenated mono heterocycle with the nitrogen atom or atoms to which they are respectively attached, or, R$_2$ and R$_3$ and/or R'$_2$ and R'$_3$ can be the same substituent, double-bonded to the nitrogen, cyclized with, respectively, R$_1$ or R'$_1$ in order to form a heterocycle, if appropriate substituted by R$_a$, which is chosen from H, alkyl, alkyl substituted by 1, 2 or 3 halogen atoms, aryl, CO—O-alkyl, CO—O-aryl, —CO—OH, —CO—NH$_2$, —CN, —CO—NH-alkyl, —CO—NH-aryl, —CO—N-(alkyl)$_2$, CO-nitrogenated heterocycle, CO-oxygenated heterocycle, CO-nitrogenated and oxygenated heterocycle, NH$_2$, NH-alkyl, N(alkyl)$_2$, nitrogenated heterocycle, oxygenated heterocycle, nitrogenated and oxygenated-heterocycle, —O-alkyl, —O-aryl, —O—CH$_2$-aryl, CH$_2$NH$_2$, CH$_2$NH-alkyl, CH$_2$N-dialkyl, CH$_2$NH-aryl, CH$_2$-nitrogenated heterocycle, CH$_2$-oxygenated heterocycle, CH$_2$-nitrogenated and oxygenated heterocycle, CH$_2$—CO—OH, or a pharmacologically acceptable salt thereof, in association with an inert pharmaceutical vehicle, with the proviso that when R$_1$ and R$_2$ form a heterocycle, and R'$_1$ and R'$_2$ form the same heterocycle as is formed with R$_1$ and R$_2$, and n=0, and R$_3$ is hydrogen or alkyl, and R'$_3$ is hydrogen or alkyl, or when R$_1$ and R$_3$ form a heterocycle, and R'$_1$ and R'$_3$ form the same heterocycle as is formed with R$_1$ and R$_3$, and n=0, and R$_2$ is hydrogen or alkyl, and R'$_2$ is hydrogen or alkyl, then m is 12-21.

2. The pharmaceutical composition according to claim 1, in a form administrable by oral route, by injectable route, or by rectal route.

3. The pharmaceutical composition of claim 1 for the treatment of malaria.

4. A pharmaceutical composition according to claim 1 wherein the pharmaceutically effective amount is an amount effective to treat malaria.

5. A pharmaceutical composition according to claim 1 wherein said at least one compound is of the formula (V)

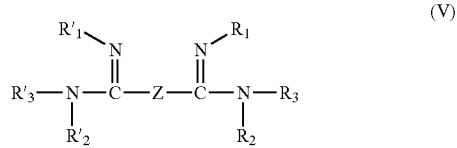 (V)

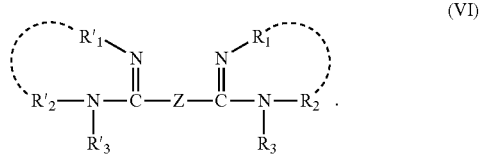 (VI)

or a pharmacologically acceptable salt thereof.

6. A pharmaceutical composition according to claim 5 wherein in said compound or pharmacologically acceptable salt thereof $R_1$, $R'_1$, $R_2$, $R'_2$, $R_3$ and $R'_3$ are independent of one another.

7. A pharmaceutical composition according to claim 6, wherein in said compound or pharmacologically acceptable salt thereof $R_1$ and/or $R'_1$ do not represent a hydrogen atom, whilst $R_3$ and/or $R'_3$, $R_2$ and/or $R'_2$, represent a hydrogen atom.

8. A pharmaceutical composition according to claim 6, wherein in said compound or pharmacologically acceptable salt thereof $R_1$ and/or $R'_1$, and $R_2$ and/or $R'_2$ represent a hydrogen atom, whilst $R_3$ and/or $R'_3$ are different from a hydrogen atom.

9. A pharmaceutical composition according to claim 5, wherein in said compound or pharmacologically acceptable salt thereof $R_1$ and $R_2$, and/or $R'_1$ and $R'_2$, or $R_2$ and $R_3$, and/or $R'_2$ and $R'_3$, or $R_1$, $R_2$ and $R_3$ and/or $R'_1$, $R'_2$ and $R'_3$ together form a heterocycle.

10. A pharmaceutical composition according to claim 9, wherein in said compound or pharmacologically acceptable salt thereof $R_1$ and $R_2$ as well as $R'_1$ and $R'_2$ form a heterocycle, of the formula (VI)

11. A pharmaceutical composition according to claim 10, wherein in said compound or pharmacologically acceptable salt thereof $R_1$ and $R_2$ and $R'_1$ and $R'_2$ represent $-(CH_2)_p-$ wherein p is an integer from 1 to 5, and $R_3$ and/or $R'_3$ represents CO—O-alkyl, CO—O-aryl, CO—O—$CH_2$-aryl, COO—CH(alkyl)-O—CO-alkyl, PO(O-alkyl)$_2$, PO(O-aryl)$_2$, alkyl or H.

12. A pharmaceutical composition according to claim 1, wherein in said compound or pharmacologically acceptable salt thereof $R_2$ and $R_3$ and/or $R'_2$ and $R'_3$ form a same substituent and form together with $R_1$ or respectively $R'_1$ a bis-oxadiazole of formula (VIII.)

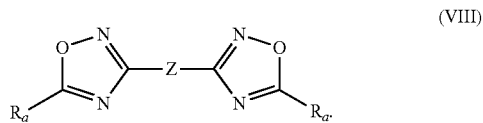 (VIII)

13. A pharmaceutical composition according to any one of claims 5-12, in a form administrable by oral route, by injectable route, or by rectal route.

14. A pharmaceutical composition of any one of claim 1, 2 or 5-12, wherein the pharmaceutically effective amount is an amount effective to treat malaria.

* * * * *